(12) United States Patent
Lisziewicz et al.

(10) Patent No.: US 7,196,186 B2
(45) Date of Patent: Mar. 27, 2007

(54) DNA COMPOSITION AND USES THEREOF

(75) Inventors: Julianna Lisziewicz, Bethesda, MD (US); Jianqing Xu, Beijing (CN); Franco Lori, Bethesda, MD (US)

(73) Assignee: Research Institute for Genetic and Human Therapy (R.I.G.H.T.), Bethesda, MD (US)

( * ) Notice: Subject to any disclaimer, the term of this patent is extended or adjusted under 35 U.S.C. 154(b) by 546 days.

(21) Appl. No.: 10/757,343

(22) Filed: Jan. 14, 2004

(65) Prior Publication Data

US 2004/0158053 A1 Aug. 12, 2004

Related U.S. Application Data

(60) Provisional application No. 60/440,245, filed on Jan. 15, 2003.

(51) Int. Cl.
- C12N 15/11 (2006.01)
- C12N 15/63 (2006.01)
- C12N 15/09 (2006.01)
- C07H 21/04 (2006.01)

(52) U.S. Cl. .................... 536/23.1; 435/320.1
(58) Field of Classification Search ............... 536/23.1; 435/320.1
See application file for complete search history.

(56) References Cited

U.S. PATENT DOCUMENTS 6,348,450 B1 2/2002 Tang et al.

6,420,176 B1 7/2002 Lisziewicz et al.

FOREIGN PATENT DOCUMENTS

| WO | WO 99/43350 | 9/1999 |
|---|---|---|
| WO | PCT/US02/16546 | 11/2002 |

OTHER PUBLICATIONS

Robinson, H.L. (2002). "New hope for an AIDS vaccine." Nature Rev Immunol 2(4): 239-250.

Fields, B. N. and D. M. Knipe, Eds. (1990). Virology. Retroviridae and their replication. New York, Raven Press, LTD.

Chen, S. S., A. A. Ferrante, et al. (1996). "Characterization of an envelope mutant of HIV-1 that interferes with viral infectivity." Virology 226(2): 260-8.

Smythe, J. A., D. Sun, et al. (1994). "A Rev-inducible mutant gag gene stably transferred into T lymphocytes: an approach to gene therapy against human immunodeficiency virus type 1 infection." Proc Natl Acad Sci U S A 91(9): 3657-61.

Yung, E., M. Sorin, et al. (2001). "Inhibition of HIV-1 virion production by a transdominant mutant of integrase interactor 1," Nat Med 7(8): 920-6.

(Continued)

Primary Examiner—Bruce R. Campell
Assistant Examiner—Nicole Kinsey
(74) Attorney, Agent, or Firm—Valerie E. Looper

(57) ABSTRACT

A plasmid DNA that encodes one or more antigenic genes operably linked to a promoter and a truncated retroviral 3' LTR exhibits both enhanced safety and acceptable efficiency of expression of antigenic proteins.

2 Claims, 9 Drawing Sheets

Composition of pLWXu1 (12,252bp)

OTHER PUBLICATIONS

Plavec, I., M. Agarwal, et al. (1997). "High transdominant RevM10 protein levels are required to inhibit HIV-1 replication in cell lines and primary T cells: implication for gene therapy of AIDS." Gene Ther 4(2): 128-39.

Fraisier, C., D. A. Abraham, et al. (1998). "Inhibition of Tat-mediated transactivation and HIV replication with Tat mutatn and repressor domain fusion proteins." Gene Ther 5(7): 946-54.

Sawaya, B. E., K. Khalili, et al. (2000). "Transdominant activity of human immunodeficiency virus type 1 Vpr with a mutation at residue R73." J Virol 74(10): 4877-81.

Gitlin, S. D., P. F. Lindholm, et al. (1991). "Transdominant human T-cell lymphotropic virus type I TAX1 mutant that fails to localize to the nucleus." J Virol 65(5): 2612-21.

Bohnlein, S., F. P. Pirker et al. (1991). "Transdominant repressors for human T-cell leukemia virus type I rex and human immunodeficiency virus type 1 rev function." J Virol 65(1): 81-8.

Smith, C. A. and N. A. DeLuca (1992). "Transdominant inhibition of herpes simplex virus growth in transgenic mice." Virology 191(2): 581-8.

Chen, J., C. Panagiotidis, et al. (1992). "Multimerization of ICP0, a herpes simplex virus immediate-early protein." J Virol 66(9): 5598-602.

Piccinini, G., A. Foli, et al. (2002). "Complimentary antiviral efficacy of hydroxyurea and protease inhibitors in human immunideficiency virus-infected dendridic cells and lyphocytes." J Virol 76(5): 2274-8.

Jayan, G.C., P. Cordelier, et al. (2001). "SV40-derived vectors provide effective transgene expression and inhibition of HIV-1 using constitutive, conditional,and pol III promoters." Gene Ther 8(13): 1033-42.

Frankel, S.S., K. Tenner-Racz, et al. (1997). "Active replication of HIV-1 at the lymphoepithelial surface of the tonsil." Am J Pathol 151(1): 89-96.

Jamieson, B. D., G. M. Aldrovandi, et al. (1994). "Requirement of human imminuodeficiency virus type 1 nef for in vivo replication and pathogenicity." J Virol 68(6): 3478-85.

Aldrovandi, G. M., L. Gao, et al. (1998). "Regions of human immunodificiency virus type 1 nef required for function in vivo." J Virol 72(9): 7032-9.

Geffin, R., D. Wolf, et al. (2000). "Functional and structural defects in HIV type 1 nef genes derived from pediatric long-term survivors." AIDS Res Hum Retroviruses 16(17): 1855-68.

Lisziewicz, J., D. I. Gabrilovich, et al. (2001). "Induction of potent human immunodificiency virus type 1-specific T-cell-restricted immunity by genetically modified dendritic cells." J Virol 75(16): 7621-8.

Zufferey, R., T. Dull, et al. (1998). "Self-inactivating lentivirus vector for safe and efficient in vivo gene delivery." J Virol 72(12): 9873-80.

Vicenzi, E., D. S. Dimitrov, et al. (1994). "An integration-defective U5 deletion mutant of human immunodeficiency virus type 1 reverts by eliminating additional long terminal repeat sequences." J Virol 68(12): 7879-90.

Zhou, H., G. J. Raniey, et al. (2001). "Substrate sequence selection by retroviral integrase." J Virol 75(3): 1359-70.

Murphy, J. E. and S. P. Goff (1989) "Construction and analysis of deletion mutations in the U5 region of Moloney murine luekemia virus: effects on RNA packaging and revers transcription." J Virol 63(1): 319-27.

Lisziewicz, J., E. Rosenberg, et al. (1999). "Control of HIV despite the discontinuation of antiretroviral therapy." N Engl J Med 340(21): 1643-4.

Lori, F., M. G. Lewis, et al. (2000). "Control of SIV rebound through structured treatment interruptions during early infection." Science 290(5496): 1591-3.

Rosenberg, E. S., M. Altfeld, et al. (2000). "Immune control of HIV-1 after early treatment of acute infection." Nature 407(6803): 523-6.

Barouch, D. H., J. Kuntsman, et al. (2002). "Eventual AIDS vaccine failure in a rhesus monkey by viral escape from cytotoxic T lymphocytes." Nature 415(6869): 335-9.

Trono, D., M. B. Feinberg, et al. (1989). "HIV-1 gag mutants can dominantly interfere with the replication of the wild-type virus." Cell 59: 113-120.

Grant, E. P., M. T. Michalek, et al. (1995). "Rate of antigen degradation by the ubiquitin-proteasome pathway influences MHC class I presentation." J Immunol 155(8): 3750-8.

Sequence features of LW (9,719bp)

Composition of pLWXu1 (12,252bp)

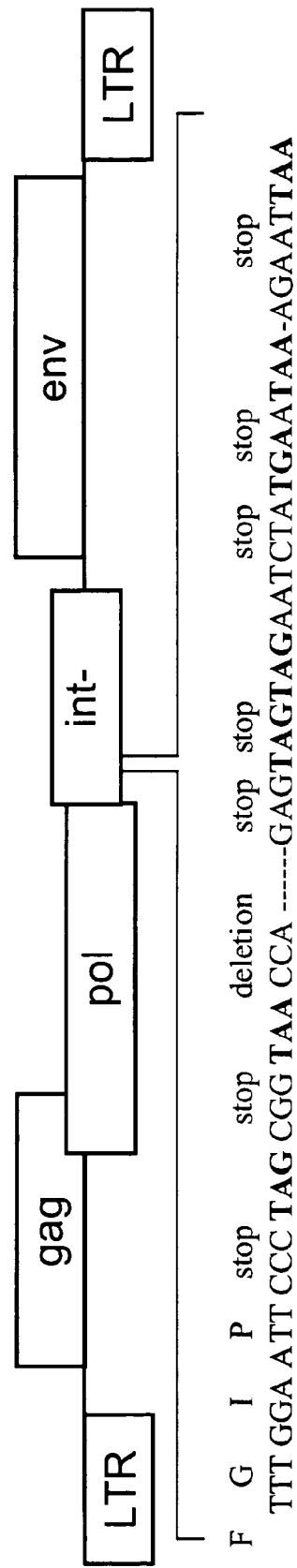
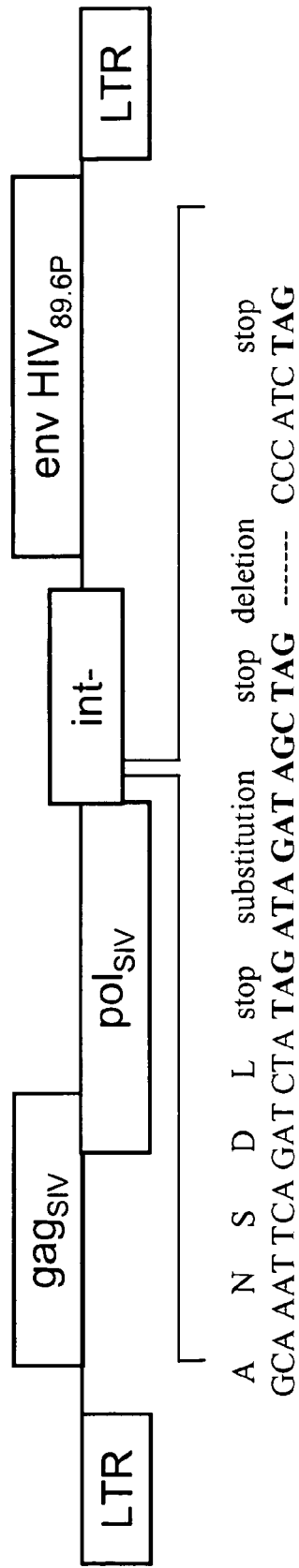
Fig. 8

SEQUENCE LISTING

```
<160> NUMBER OF SEQ ID NOS: 4

<210> SEQ ID NO 1
<211> LENGTH: 9719
<212> TYPE: DNA
<213> ORGANISM: Human immunodeficiency virus type 1
<220> FEATURE:
<221> NAME/KEY: LTR
<222> LOCATION: (1)..(630)
<223> OTHER INFORMATION: 5' LTR
<220> FEATURE:
<221> NAME/KEY: LTR
<222> LOCATION: (9083)..(9719)
<223> OTHER INFORMATION: 3' LTR
<220> FEATURE:
<221> NAME/KEY: gene
<222> LOCATION: (8794)..(9414)
<223> OTHER INFORMATION: Nef
<220> FEATURE:
<221> NAME/KEY: protein_bind
<222> LOCATION: (7723)..(8076)
<223> OTHER INFORMATION: RRE
<220> FEATURE:
<221> NAME/KEY: gene
<222> LOCATION: (6222)..(8792)
<223> OTHER INFORMATION: Env
<220> FEATURE:
<221> NAME/KEY: gene
<222> LOCATION: (6062)..(6307)
<223> OTHER INFORMATION: Vpu
<220> FEATURE:
<221> NAME/KEY: gene
<222> LOCATION: (8376)..(8650)
<223> OTHER INFORMATION: Rev2
<220> FEATURE:
<221> NAME/KEY: gene
<222> LOCATION: (5970)..(6045)
<223> OTHER INFORMATION: Rev1
<220> FEATURE:
<221> NAME/KEY: gene
<222> LOCATION: (8376)..(8466)
<223> OTHER INFORMATION: Tat2
<220> FEATURE:
<221> NAME/KEY: gene
<222> LOCATION: (5831)..(6045)
<223> OTHER INFORMATION: Tat1
<220> FEATURE:
<221> NAME/KEY: gene
<222> LOCATION: (5560)..(5850)
<223> OTHER INFORMATION: Vpr
<220> FEATURE:
<221> NAME/KEY: gene
<222> LOCATION: (5042)..(5620)
<223> OTHER INFORMATION: Vif
<220> FEATURE:
<221> NAME/KEY: gene
<222> LOCATION: (2086)..(5097)
<223> OTHER INFORMATION: polymerase: protease, reverse transcriptase,
      integrase
<220> FEATURE:
<221> NAME/KEY: gene
<222> LOCATION: (791)..(2293)
<223> OTHER INFORMATION: Gag
<220> FEATURE:
<221> NAME/KEY: stem_loop
<222> LOCATION: (456)..(531)
<223> OTHER INFORMATION:

<400> SEQUENCE: 1
```

-continued

```
tggaagggct aattcactcc aacgaagac aagatatcct tgatctgtgg atctaccaca      60
cacaaggcta cttccctgat tggcagaact acacaccagg accagggatc agatatccac    120
tgacctttgg atggtgctac aagctagtac cagttgagcc agagaagtta aagaagcca     180
acaaaggaga gaacaccagc ttgttacacc ctgtgagcct gcatggaatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt ccagggagg cgtggcctgg gcgggactgg ggagtggcga gccctcagat     420
cctgcatata agcagctgct ttttgcctgt actgggtctc tctggttaga ccagatctga    480
gcctgggagc tctctggcta gctagggaac ccactgctta agcctcaata agcttgcct     540
tgagtgcttc aagtagtgtg tgcccgtctg ttgtgtgact ctggtaacta gagatccctc    600
agaccctttt agtcagtgtg gaaaatctct agcagtggcg cccgaacagg gacctgaaag    660
cgaaagggaa accagaggag ctctctcgac gcaggactcg gcttgctgaa gcgcgcacgg    720
caagaggcga ggggcggcga ctggtgagta cgccaaaaaa ttttgactag cggaggctag    780
aaggagagag atgggtgcga gagcgtcagt attaagcggg ggaaaattag atcgatggga    840
aaaaattcgg ttaaggccag ggggaaagaa aaatataaa ttaaaacata tagtatgggc     900
aagcagggag ctagaacgat tcgcagttaa tcctggcctg ttagaaacat cagaaggctg    960
tagacaaata ctgggacagc tacaaccatc ccttcagaca ggatcagaag aatgtagatc   1020
attatataat acagtagcaa ccctctattg tgtgcatcaa aggatagaga taaaagacac   1080
caaggaagct ttagacaaga taaggaaga gcaaaacaaa agtaagaaaa aagcacagca   1140
agcagcagct gacacaggac acagcagtca ggtcagccaa aattacccta tagtgcagaa   1200
catccagggg caaatggtac atcaggccat atcacctaga actttaaatg catgggtaaa   1260
agtagtagaa gagaaggctt tcagcccaga agtaataccc atgttttcag cattatcaga   1320
aggagccacc ccacaagatt taaacaccat gctaaacaca gtggggggac atcaagcagc   1380
catgcaaatg ttaaaagaga ccatcaatga ggaagctgca gaatgggata gagtgcatcc   1440
agtgcatgca gggcctatcg caccaggcca gatgagagaa ccaaggggaa gtgacatagc   1500
aggaactact agtaccccttc aggaacaaat aggatggatg acaaataatc cacctatccc   1560
agtaggagaa atttataaaa gatggataat cctgggatta aataagatag taagaatgta   1620
tagccctacc agcattctgg acataagaca aggaccaaaa gaacctttta gagactatgt   1680
agaccggttc tataaaactc taagagccga gcaagcttca caggaggtaa aaaattggat   1740
gacagaaacc ttgttggtcc aaaatgcgaa cccagattgt aagactattt taaaagcatt   1800
gggaccagca gctacattag aagaaatgat gacagcatgt cagggagtgg gaggacccgg   1860
ccataaggca agagttttgg ctgaagcaat gagccaagta acaaattcag ctaccataat   1920
gatgcagaga ggcaattttta ggaaccaaag aaagattgtt aagtgtttca attgtggcaa   1980
agaagggcac atagccagaa attgcagggc ccctaggaaa aagggctgtt ggaaatgtgg   2040
aaaggaagga caccaaatga aagattgtac tgagagacag gctaatttttt tagggaagat   2100
ctggccttcc tacaagggaa ggccagggaa ttttcttcag agcagaccag agccaacagc   2160
cccaccagaa gagagcttca ggtctggggt agagacaaca actcccccctc agaagcagga   2220
gccgatagac aaggaactgt atcctttaac ttccctcaga tcactctttg gcaacgaccc   2280
ctcgtcacaa taaagatagg ggggcaacta aaggaagctc tattagatac aggagcagat   2340
gatacagtat tagaagaaat gagtttgcca ggaagatgga aaccaaaaat gatagggga    2400
```

```
attggaggtt ttatcaaagt aagacagtat gatcagatac tcatagaaat ctgtggacat   2460
aaagctatag gtacagtatt agtaggacct acacctgtca acataattgg aagaaatctg   2520
ttgactcaga ttggttgcac tttaaatttt cccattagcc ctattgagac tgtaccagta   2580
aaattaaagc caggaatgga tggcccaaaa gttaaacaat ggccattgac agaagaaaaa   2640
ataaaagcat tagtagaaat ttgtacagaa atggaaaagg aagggaaaat ttcaaaaatt   2700
gggcctgaaa atccatacaa tactccagta tttgccataa agaaaaaaga cagtactaaa   2760
tggagaaaat tagtagattt cagagaactt aataagagaa ctcaagactt ctgggaagtt   2820
caattaggaa taccacatcc cgcagggtta aaaagaaaaa aatcagtaac agtactggat   2880
gtgggtgatg catatttttc agttccctta gatgaagact tcaggaagta tactgcattt   2940
accataccta gtataaacaa tgagacacca gggattagat atcagtacaa tgtgcttcca   3000
cagggatgga aaggatcacc agcaatattc caaagtagca tgacaaaaat cttagagcct   3060
tttagaaaac aaaatccaga catagttatc tatcaataca tggatgattt gtatgtagga   3120
tctgacttag aaatagggca gcatagaaca aaaatagagg agctgagaca acatctgttg   3180
aggtggggac ttaccacacc agacaaaaaa catcagaaag aacctccatt cctttggatg   3240
ggttatgaac tccatcctga taaatggaca gtacagccta tagtgctgcc agaaaaagac   3300
agctggactg tcaatgacat acagaagtta gtggggaaat tgaattgggc aagtcagatt   3360
tacccaggga ttaaagtaag gcaattatgt aaactcctta gaggaaccaa agcactaaca   3420
gaagtaatac cattaacaga agaagcagag ctagaactgg cagaaaacag agagattcta   3480
aaagaaccag tacatggagt gtattatgac ccatcaaaag acttaatagc agaaatacag   3540
aagcaggggc aaggccaatg gacatatcaa atttatcaag agccatttaa aaatctgaaa   3600
acaggaaaat atgcaagaat gagggggtacc cacactaatg atgtaaaaca attaacagag   3660
gcagtgcaaa aaataaccac cgaaagcata gtaatatggg gaaagactcc taaatttaaa   3720
ctacccatac aaaaggaaac atgggaaaca tggtggacag agtattggca agccacctgg   3780
attcctgagt gggagtttgt caatacccct ccttagtga aattatggta ccagttagag   3840
aaagaaccca tagtaggagc agaaaccttc tatgtagatg gggcagctaa cagggagact   3900
aaattaggaa aagcaggata tgttactaac aaaggaagac aaaaggttgt ccccctaact   3960
aacacaacaa atcagaaaac tgagttacaa gcaatttatc tagctttgca ggattcagga   4020
ttagaagtaa acatagtaac agactcacaa tatgcattag gaatcattca agcacaacca   4080
gataaaagtg aatcagagtt agtcaatcaa ataatagagc agttaataaa aaaggaaaag   4140
gtctatctgg catgggtacc agcacacaaa ggaattggag gaaatgaaca agtagataaa   4200
ttagtcagtg ctggaatcag gaaaatacta ttttagatg gaatagataa ggcccaagat   4260
gaacatgaga aatatcacag taattggaga gcaatggcta gtgattttaa cctgccacct   4320
gtagtagcaa aagaaatagt agccagctgt gataaatgtc agctaaaagg agaagccatg   4380
catggacaag tagactgtag tccaggaata tggcaactag attgtacaca tttagaagga   4440
aaagttatcc tggtagcagt tcatgtagcc agtggatata tagaagcaga agttattcca   4500
gcagaaacag ggcaggaaac agcatatttt cttttaaaat tagcaggaag atggccagta   4560
aaaacaatac atacagacaa tggcagcaat ttcaccagtg ctacggttaa ggccgcctgt   4620
tggtgggcgg gaatcaagca ggaatttgga attccctaca atccccaaag tcaaggagta   4680
gtagaatcta tgaataaaga attaaagaaa attataggac aggtaagaga tcaggctgaa   4740
```

```
catcttaaga cagcagtaca aatggcagta ttcatccaca attttaaaag aaaaggggggg   4800
attgggggggt acagtgcagg ggaaagaata gtagacataa tagcaacaga catacaaact   4860
aaagaattac aaaaacaaat tacaaaaatt caaaatttc gggtttatta cagggacagc    4920
agaaatccac tttgaaaagg accagcaaag ctcctctgga aaggtgaagg ggcagtagta   4980
atacaagata atagtgacat aaaagtagtg ccaagaagaa aagcaaagat cattagggat   5040
tatggaaaac agatggcagg tgatgattgt gtggcaagta gacaggatga ggattagaac   5100
atggaaaagt ttagtaaaac accatatgta tgtttcaggg aaagctaggg gatggttta   5160
tagacatcac tatgaaagcc cttatccaag aataagttca gaagtacaca tcccactagg   5220
ggatgctaga ttggtaataa caacatattg gggtctgcat acaggagaaa gagactggca   5280
tttgggtcag ggagtctcca tagaatggag gaaaaagaga tatagcacac aagtagaccc   5340
tgaactagca gaccaactaa ttcatctgta ttactttgac tgtttttcag actctgctat   5400
aagaaaggcc ttattaggac acatagttag ccctaggtgt gaatatcaag caggacataa   5460
caaggtagga tctctacaat acttggcact agcagcatta ataacaccaa aaaagataaa   5520
gccacctttg cctagtgtta cgaaactgac agaggataga tggaacaagc cccagaagac   5580
caagggccac agagggagcc acacaatgaa tggacactag agcttttaga ggagcttaag   5640
aatgaagctg ttagacattt tcctaggatt tggctccatg gcttaggggca acatatctat   5700
gaaacttatg gggatacttg ggcaggagtg gaagccataa taagaattct gcaacaactg   5760
ctgtttaccc atttcagaat tgggtgtcga catagcagaa taggcgttac tcgacagagg   5820
agagcaagaa atggagccag tagatcctag actagagcct tggaagcatc caggaagtca   5880
gcctaaaact gcttgtacca attgctattg taaaaagtgt tgctttcatt gccaagtttg   5940
tttcataaca aaagccttag gcatctccta tggcaggaag aagcggagac agcgacgaag   6000
acctcctcaa agcagtcaga ctcatcaagt ttctctatca aagcagtaag tagtacatgt   6060
aatgcaacct atacaaatag caatagtagc attagtagta gcaataataa tagcaatagt   6120
tgtgtggtcc atagtaatca tagaatatag gaaaatatta agacaaagaa aaatagacag   6180
gttaattgat agactaatag aaagagcaga agacagtggc aatgagagtg aaggagaaat   6240
atcagcactt gcggagatgg gggtggagat ggggcaccat gctccttggg atgttgatga   6300
tttgtagtgc tacagaaaaa ttgtgggtca cagtctatta tggggtacct gtgtggaagg   6360
aagcaaccac cactctattt tgtgcatcag atgctaaagc atatgataca gaggtacata   6420
atgtttgggc cacacatgcc tgtgtaccca cagaccccaa cccacaagaa gtagtattgg   6480
taaatgtgac agaaaatttt aacatgtgga aaaatgatat ggtagaacag atgcatgagg   6540
atataatcag tttatgggat caaagcctaa agccatgtgt aaaattaacc ccactctgtg   6600
ttagttttaaa gtgcactgat ttgaagaatg atactaatac caatagtagt agcggggggaa   6660
tgataatgga gaaggagag ataaaaaact gctctttcaa tatcagcaca agcataagag   6720
gtaaggtgca gaaagaatat gcatttttt ataaacatga tataatacca atagataatg   6780
atactaccag ctatacgttg acaagttgta acacctcagt cattacacag gcctgtccaa   6840
aggtatcctt tgagccaatt cccatacatt attgtgcccc ggctggtttt gcgattctaa   6900
aatgtaataa taagacgttc aatggaacag gaccatgtac aaatgtcagc acagtacaat   6960
gtacacatgg aattaagcca gtagtatcaa ctcaactgct gttaaatggc agtctagcag   7020
aagaagaggt agtaattaga tctgccaatc tcacagacaa tgttaaaacc ataatagtac   7080
agctgaacca atctgtagaa attaattgta caagacccaa caacaataca agaaaaagaa   7140
```

-continued

```
tccgtatcca gagaggacca gggagaacat tgttacaat aggaaaaata ggaaatatga    7200
gacaagcaca ttgtaacatt agtagagcaa atggaataa cactttaaaa cagatagcta    7260
gcaaattaag agaacaatat ggaaataata aaacaataat ctttaagcag tcctcaggag    7320
gggacctaga aattgtaacg cacagttta attgtggagg ggaattttc tactgtaatt     7380
caacacaact gtttaatagt acttggtta atagtacttg gagtactgaa gggtcaaata    7440
acactgaagg aagtgacaca atcacactcc catgcagaat aaaacaaatt ataaacatgt   7500
ggcaggaagt aggaaaagca atgtatgccc ctcccatcag cggacaaatt agatgttcat   7560
caaatattac agggctgcta ttaacaagag atggtggtaa taacaacaat gggtccgaga   7620
tcttcagacc tggaggagga gatatgaggg acaattggag aagtgaatta tataaatata   7680
aagtagtaaa aattgaacca ttaggagtag caccccaccaa ggcaaagaga agagtggtgc   7740
agagagaaaa aagagcagtg ggaataggag ctttgttcct tgggttcttg ggagcagcag   7800
gaagcactat gggcgcagcg tcaatgacgc tgacggtaca ggccagacaa ttattgtctg   7860
gtatagtgca gcagcagaac aatttgctga gggctattga ggcgcaacag catctgttgc   7920
aactcacagt atggggcatc aagcagctcc aggcaagaat cctggctgtg gaaagatacc   7980
taaaggatca acagctcctg gggatttggg gttgctctgg aaaactcatt tgcaccactg   8040
ctgtgccttg gaatgctagt tggagtaata atctctgga acagatttgg aatcacacga   8100
cctggatgga gtgggacaga gaattaaca attacacaag cttaatacac tccttaattg   8160
aagaatcgca aaaccaacaa gaaaagaatg aacaagaatt attggaatta gataaatggg   8220
caagtttgtg gaattggttt aacataacaa attggctgtg gtatataaaa atattcataa   8280
tgatagtagg aggcttggta ggtttaagaa tagttttgc tgtactttct atagtgaata   8340
gagttaggca gggacattca ccattatcgt ttcagaccca cctcccaacc ccggggggac   8400
ccgacaggcc cgaaggaata aagaagaag gtggagagag acagagac agatccattc      8460
gattagtgaa cggatcctta gcacttatct gggacgatct gcgaagcctg tgcctcttca   8520
gctaccaccg cttgagagac ttactcttga ttgtaacgag gattgtggaa cttctgggac   8580
gcagggggtg ggaagccctc aaatattggt ggaatctcct acagtattgg agtcaggaac   8640
taaagaatag tgctgttagc ttgctcaatg ccacagccat agcagtagct gaggggacag   8700
ataggggttat agaagtagta caaggagctt gtagagctat tcgccacata cctagaagaa   8760
taagacaggg cttggaaagg attttgctat aagatgggtg gcaagtggtc aaaaagtagt   8820
gtgattggat ggcctactgt aagggaaaga atgagacgag ctgagccagc agcagatggg   8880
gtgggagcag catctcaaga cctggaaaaa catggagcaa tcacaagtag caatacagca   8940
gctaccaatg ctgattgtgc ctggctagaa gcacaagagg aggaggaggt gggttttcca   9000
gtcacacctc aggtaccttt aagaccaatg acttacaagg cagctgtaga tcttagccac   9060
tttttaaaag aaaagggggg actggaaggg ctaattcact cccaacgaag acaagatatc   9120
cttgatctgt ggatctacca cacacaaggc tacttccctg attggcagaa ctacacacca   9180
ggaccaggga tcagatatcc actgaccttt ggatggtgct acaagctagt accagttgag   9240
ccagagaagt tagaagaagc caacaaagga gaaacacca gcttgttaca ccctgtgagc    9300
ctgcatggaa tggatgaccc ggagagaga gtgttagagt ggaggtttga cagccgccta    9360
gcatttcatc acgtgcccg agagctgcat ccggagtact tcaagaactg ctgatatcga   9420
gcttgctaca agggactttc cgctggggac tttccaggga ggcgtggcct gggcgggact   9480
```

```
ggggagtggc gagccctcag atcctgcata taagcagctg cttttttgcct gtactgggtc    9540 tctctggtta gaccagatct gagcctggga gctctctggc tagctaggga acccactgct    9600
taagcctcaa taaagcttgc cttgagtgct tcaagtagtg tgtgcccgtc tgttgtgtga    9660
ctctggtaac tagagatccc tcagacccctt ttagtcagtg tggaaaatct ctagcaggt    9719
```

```
<210> SEQ ID NO 2
<211> LENGTH: 9719
<212> TYPE: DNA
<213> ORGANISM: Human immunodeficiency virus type 1
<220> FEATURE:
<221> NAME/KEY: LTR
<222> LOCATION: (1)..(630)
<223> OTHER INFORMATION: 5' LTR
<220> FEATURE:
<221> NAME/KEY: LTR
<222> LOCATION: (9083)..(9243)
<223> OTHER INFORMATION: truncated 3' LTR
<220> FEATURE:
<221> NAME/KEY: gene
<222> LOCATION: (8794)..(9246)
<223> OTHER INFORMATION: truncated Nef
<220> FEATURE:
<221> NAME/KEY: protein_bind
<222> LOCATION: (7723)..(8076)
<223> OTHER INFORMATION: RRE
<220> FEATURE:
<221> NAME/KEY: gene
<222> LOCATION: (6222)..(8792)
<223> OTHER INFORMATION: Env
<220> FEATURE:
<221> NAME/KEY: gene
<222> LOCATION: (6062)..(6307)
<223> OTHER INFORMATION: Vpu
<220> FEATURE:
<221> NAME/KEY: gene
<222> LOCATION: (8376)..(8650)
<223> OTHER INFORMATION: Rev2
<220> FEATURE:
<221> NAME/KEY: gene
<222> LOCATION: (5970)..(6045)
<223> OTHER INFORMATION: Rev1
<220> FEATURE:
<221> NAME/KEY: gene
<222> LOCATION: (8376)..(8466)
<223> OTHER INFORMATION: Tat2
<220> FEATURE:
<221> NAME/KEY: gene
<222> LOCATION: (5831)..(6045)
<223> OTHER INFORMATION: Tat1
<220> FEATURE:
<221> NAME/KEY: gene
<222> LOCATION: (5560)..(5850)
<223> OTHER INFORMATION: Vpr
<220> FEATURE:
<221> NAME/KEY: gene
<222> LOCATION: (5042)..(5620)
<223> OTHER INFORMATION: Vif
<220> FEATURE:
<221> NAME/KEY: gene
<222> LOCATION: (2086)..(5097)
<223> OTHER INFORMATION: polymerase: protease, reverse transcriptase,
      integrase
<220> FEATURE:
<221> NAME/KEY: mutation
<222> LOCATION: (4657)..(4659)
<223> OTHER INFORMATION: stop codon inserted
<220> FEATURE:
<221> NAME/KEY: mutation
<222> LOCATION: (4663)..(4665)
<223> OTHER INFORMATION: stop codon inserted
<220> FEATURE:
<221> NAME/KEY: mutation
<222> LOCATION: (4669)..(4675)
<223> OTHER INFORMATION: 7 base pair deletion
<220> FEATURE:
```

```
<221> NAME/KEY: mutation
<222> LOCATION: (4679)..(4684)
<223> OTHER INFORMATION: 2 stop  codons inserted
<220> FEATURE:
<221> NAME/KEY: mutation
<222> LOCATION: (4691)..(4693)
<223> OTHER INFORMATION: stop  codon inserted
<220> FEATURE:
<221> NAME/KEY: mutation
<222> LOCATION: (4703)..(4705)
<223> OTHER INFORMATION: stop  codon inserted
<220> FEATURE:
<221> NAME/KEY: mutation
<222> LOCATION: (21)..(21)
<223> OTHER INFORMATION: 1 base pair deletion
<220> FEATURE:
<221> NAME/KEY: mutation
<222> LOCATION: (9244)..(9246)
<223> OTHER INFORMATION: stop codon inserted
<220> FEATURE:
<221> NAME/KEY: mutation
<222> LOCATION: (104)..(104)
<223> OTHER INFORMATION: point mutation from A to G
<220> FEATURE:
<221> NAME/KEY: mutation
<222> LOCATION: (473)..(473)
<223> OTHER INFORMATION: point mutation from A to G
<220> FEATURE:
<221> NAME/KEY: mutation
<222> LOCATION: (8872)..(8872)
<223> OTHER INFORMATION: point mutation from G to C
<220> FEATURE:
<221> NAME/KEY: mutation
<222> LOCATION: (8985)..(8985)
<223> OTHER INFORMATION: point mutation from G to A
<220> FEATURE:
<221> NAME/KEY: mutation
<222> LOCATION: (9017)..(9017)
<223> OTHER INFORMATION: point mutation from C to T
<220> FEATURE:
<221> NAME/KEY: gene
<222> LOCATION: (2086)..(5090)
<223> OTHER INFORMATION: polymerase: protease, reverse transcriptase,
      integrase
<220> FEATURE:
<221> NAME/KEY: gene
<222> LOCATION: (791)..(2293)
<223> OTHER INFORMATION: Gag
<220> FEATURE:
<221> NAME/KEY: stem_loop
<222> LOCATION: (456)..(531)
<223> OTHER INFORMATION: TAR

<400> SEQUENCE: 2
```

| | | | | |
|---|---|---|---|---|
| tggaagggct | aattcactcc | caacgaagac | aagatatcct | tgatctgtgg | atctaccaca | 60 |
| cacaaggcta | cttccctgat | tggcagaact | acacaccagg | accagggatc | agatatccac | 120 |
| tgacctttgg | atggtgctac | aagctagtac | cagttgagcc | agagaagtta | gaagaagcca | 180 |
| acaaaggaga | gaacaccagc | ttgttacacc | ctgtgagcct | gcatggaatg | gatgacccgg | 240 |
| agagagaagt | gttagagtgg | aggtttgaca | gccgcctagc | atttcatcac | gtggcccgag | 300 |
| agctgcatcc | ggagtacttc | aagaactgct | gatatcgagc | ttgctacaag | ggactttccg | 360 |
| ctggggactt | tccagggagg | cgtggcctgg | gcgggactgg | ggagtggcga | gccctcagat | 420 |
| cctgcatata | agcagctgct | ttttgcctgt | actgggtctc | tctggttaga | ccagatctga | 480 |
| gcctgggagc | tctctggcta | gctagggaac | ccactgctta | agcctcaata | aagcttgcct | 540 |
| tgagtgcttc | aagtagtgtg | tgcccgtctg | ttgtgtgact | ctggtaacta | gagatccctc | 600 |
| agacccttttt | agtcagtgtg | gaaaatctct | agcagtggcg | cccgaacagg | gacctgaaag | 660 |
| cgaaagggaa | accagaggag | ctctctcgac | gcaggactcg | gcttgctgaa | gcgcgcacgg | 720 |

-continued

```
caagaggcga ggggcggcga ctggtgagta cgccaaaaaa ttttgactag cggaggctag      780
aaggagagag atgggtgcga gagcgtcagt attaagcggg ggaaaattag atcgatggga      840
aaaaattcgg ttaaggccag ggggaaagaa aaaatataaa ttaaaacata tagtatgggc      900
aagcagggag ctagaacgat tcgcagttaa tcctggcctg ttagaaacat cagaaggctg      960
tagacaaata ctgggacagc tacaaccatc ccttcagaca ggatcagaag aatgtagatc     1020
attatataat acagtagcaa ccctctattg tgtgcatcaa aggatagaga taaaagacac     1080
caaggaagct ttagacaaga taaaggaaga gcaaaacaaa agtaagaaaa aagcacagca     1140
agcagcagct gacacaggac acagcagtca ggtcagccaa aattacccta tagtgcagaa     1200
catccagggg caaatggtac atcaggccat atcacctaga actttaaatg catgggtaaa     1260
agtagtagaa gagaaggctt tcagcccaga agtaataccc atgttttcag cattatcaga     1320
aggagccacc ccacaagatt taaacaccat gctaaacaca gtggggggac atcaagcagc     1380
catgcaaatg ttaaaagaga ccatcaatga ggaagctgca gaatgggata gagtgcatcc     1440
agtgcatgca gggcctatcg caccaggcca gatgagagaa ccaaggggaa gtgacatagc     1500
aggaactact agtacccttc aggaacaaat aggatggatg acaaataatc cacctatccc     1560
agtaggagaa atttataaaa gatggataat cctgggatta aataagatag taagaatgta     1620
tagccctacc agcattctgg acataagaca aggaccaaaa gaacctttta gagactatgt     1680
agaccggttc tataaaactc taagagccga gcaagcttca caggaggtaa aaaattggat     1740
gacagaaacc ttgttggtcc aaaatgcgaa cccagattgt aagactattt taaaagcatt     1800
gggaccagca gctacattag aagaaatgat gacagcatgt cagggagtgg gaggacccgg     1860
ccataaggca agagttttgg ctgaagcaat gagccaagta acaaattcag ctaccataat     1920
gatgcagaga ggcaatttta ggaaccaaag aaagattgtt aagtgtttca attgtggcaa     1980
agaagggcac atagccagaa attgcagggc ccctaggaaa aagggctgtt ggaaatgtgg     2040
aaaggaagga caccaaatga aagattgtac tgagagacag gctaattttt tagggaagat     2100
ctggccttcc tacaagggaa ggccaggaa ttttcttcag agcagaccag agccaacagc     2160
cccaccagaa gagagcttca ggtctggggt agagacaaca actcccccte agaagcagga     2220 gccgatagac aaggaactgt atcctttaac ttccctcaga tcactctttg gcaacgaccc     2280
ctcgtcacaa taaagatagg ggggcaacta aaggaagctc tattagatac aggagcagat     2340
gatacagtat tagaagaaat gagtttgcca ggaagatgga aaccaaaaat gataggggga     2400
attggaggtt ttatcaaagt aagacagtat gatcagatac tcatagaaat ctgtggacat     2460
aaagctatag gtacagtatt agtaggacct acacctgtca acataattgg aagaaatctg     2520
ttgactcaga ttggttgcac tttaaatttt cccattagcc ctattgagac tgtaccagta     2580
aaattaaagc caggaatgga tggcccaaaa gttaaacaat ggccattgac agaagaaaaa     2640
ataaaagcat tagtagaaat ttgtacagaa atggaaaagg aagggaaaat ttcaaaaatt     2700
gggcctgaaa atccatacaa tactccagta tttgccataa agaaaaaaga cagtactaaa     2760
tggagaaaat tagtagattt cagagaactt aataagagaa ctcaagactt ctgggaagtt     2820
caattaggaa taccacatcc cgcagggtta aaaagaaaa aatcagtaac agtactggat     2880
gtgggtgatg catatttttc agttccctta gatgaagact tcaggaagta tactgcattt     2940
accataccta gtataaacaa tgagacacca gggattagat atcagtacaa tgtgcttcca     3000
cagggatgga aaggatcacc agcaatattc caaagtagca tgacaaaaat cttagagcct     3060
tttagaaaac aaaatccaga catagttatc tatcaataca tggatgattt gtatgtagga     3120
```

```
tctgacttag aaataggggca gcatagaaca aaaatagagg agctgagaca acatctgttg   3180
aggtggggac ttaccacacc agacaaaaaa catcagaaag aacctccatt cctttggatg   3240
ggttatgaac tccatcctga taaatggaca gtacagccta tagtgctgcc agaaaaagac   3300
agctggactg tcaatgacat acagaagtta gtggggaaat tgaattgggc aagtcagatt   3360
tacccaggga ttaaagtaag gcaattatgt aaactcctta gaggaaccaa agcactaaca   3420
gaagtaatac cattaacaga agaagcagag ctagaactgg cagaaaacag agagattcta   3480
aaagaaccag tacatggagt gtattatgac ccatcaaaag acttaatagc agaaatacag   3540
aagcagggc aaggccaatg gacatatcaa atttatcaag agccatttaa aaatctgaaa   3600
acaggaaaat atgcaagaat gaggggtacc cacactaatg atgtaaaaca attaacagag   3660
gcagtgcaaa aaataaccac cgaaagcata gtaatatggg gaaagactcc taaatttaaa   3720
ctacccatac aaaaggaaac atgggaaaca tggtggacag agtattggca agccacctgg   3780
attcctgagt gggagtttgt caatacccct cctttagtga aattatggta ccagttagag   3840
aaagaaccca tagtaggagc agaaaccttc tatgtagatg gggcagctaa cagggagact   3900
aaattaggaa aagcaggata tgttactaac aaaggaagac aaaaggttgt cccccctaact   3960
aacacaacaa atcagaaaac tgagttacaa gcaatttatc tagctttgca ggattcagga   4020
ttagaagtaa acatagtaac agactcacaa tatgcattag gaatcattca agcacaacca   4080
gataaaagtg aatcagagtt agtcaatcaa ataatagagc agttaataaa aaaggaaaag   4140
gtctatctgg catgggtacc agcacacaaa ggaattggag gaaatgaaca agtagataaa   4200
ttagtcagtg ctggaatcag gaaaatacta ttttagatg gaatagataa ggcccaagat   4260
gaacatgaga aatatcacag taattggaga gcaatggcta gtgattttaa cctgccacct   4320
gtagtagcaa aagaaatagt agccagctgt gataaatgtc agctaaaagg agaagccatg   4380
catggacaag tagactgtag tccaggaata tggcaactag attgtacaca tttagaagga   4440
aaagttatcc tggtagcagt tcatgtagcc agtggatata tagaagcaga agttattcca   4500
gcagaaacag ggcaggaaac agcatatttt cttttaaaat tagcaggaag atggccagta   4560
aaaacaatac atacagacaa tggcagcaat ttcaccagtg ctacggttaa ggccgcctgt   4620
tggtgggcgg gaatcaagca ggaatttgga attccctaca atccccaaag tcaaggagta   4680
gtagaatcta tgaataaaga attaaagaaa attataggac aggtaagaga tcaggctgaa   4740
catcttaaga cagcagtaca aatggcagta ttcatccaca attttaaaag aaaagggggg   4800
attggggggt acagtgcagg ggaaagaata gtagacataa tagcaacaga catacaaact   4860
aaagaattac aaaaacaaat tacaaaaatt caaaattttc gggtttatta cagggacagc   4920
agaaatccac tttggaaagg accagcaaag ctcctctgga aggtgaagg ggcagtagta   4980
atacaagata atagtgacat aaaagtagtg ccaagaagaa aagcaaagat cattagggat   5040
tatggaaaac agatggcagg tgatgattgt gtggcaagta gacaggatga ggattagaac   5100
atggaaaagt ttagtaaaac accatatgta tgtttcaggg aaagctaggg gatggttttta   5160
tagacatcac tatgaaagcc cttatccaag aataagttca gaagtacaca tcccactagg   5220
ggatgctaga ttggtaataa caacatattg gggtctgcat acaggagaaa gagactggca   5280
tttgggtcag ggagtctcca tagaatggag gaaaaagaga tatagcacac aagtagaccc   5340
tgaactagca gaccaactaa ttcatctgta ttactttgac tgtttttcag actctgctat   5400
aagaaaggcc ttattaggac acatagttag ccctaggtgt gaatatcaag caggacataa   5460
```

```
caaggtagga tctctacaat acttggcact agcagcatta ataacaccaa aaaagataaa    5520
gccacctttg cctagtgtta cgaaactgac agaggataga tggaacaagc cccagaagac    5580
caagggccac agagggagcc acacaatgaa tggacactag agcttttaga ggagcttaag    5640
aatgaagctg ttagacattt tcctaggatt tggctccatg gcttagggca acatatctat    5700
gaaacttatg gggatacttg gcaggagtg gaagccataa taagaattct gcaacaactg    5760
ctgtttaccc atttcagaat tgggtgtcga catagcagaa taggcgttac tcgacagagg    5820
agagcaagaa atggagccag tagatcctag actagagcct tggaagcatc caggaagtca    5880
gcctaaaact gcttgtacca attgctattg taaaaagtgt tgctttcatt gccaagtttg    5940
tttcataaca aaagccttag gcatctccta tggcaggaag aagcggagac agcgacgaag    6000
acctcctcaa agcagtcaga ctcatcaagt ttctctatca aagcagtaag tagtacatgt    6060
aatgcaacct atacaaatag caatagtagc attagtagta gcaataataa tagcaatagt    6120
tgtgtggtcc atagtaatca tagaatatag gaaaatatta agacaaagaa aaatagacag    6180
gttaattgat agactaatag aaagagcaga agacagtggc aatgagagtg aaggagaaat    6240
atcagcactt gcggagatgg gggtggagat ggggcaccat gctccttggg atgttgatga    6300
tttgtagtgc tacagaaaaa ttgtgggtca cagtctatta tggggtacct gtgtggaagg    6360
aagcaaccac cactctattt tgtgcatcag atgctaaagc atatgataca gaggtacata    6420
atgtttgggc cacacatgcc tgtgtaccca cagaccccaa cccacaagaa gtagtattgg    6480
taaatgtgac agaaaatttt aacatgtgga aaaatgatat ggtagaacag atgcatgagg    6540
atataatcag tttatgggat caaagcctaa agccatgtgt aaaattaacc ccactctgtg    6600
ttagtttaaa gtgcactgat ttgaagaatg atactaatac caatagtagt agcgggggaa    6660
tgataatgga gaaggagag ataaaaaact gctctttcaa tatcagcaca agcataagag    6720
gtaaggtgca gaaagaatat gcattttttt ataaacatga taatatacca atagataatg    6780
atactaccag ctatacgttg acaagttgta acacctcagt cattacacag gcctgtccaa    6840
aggtatcctt tgagccaatt cccatacatt attgtgcccc ggctggtttt gcgattctaa    6900
aatgtaataa taagacgttc aatggaacag gaccatgtac aaatgtcagc acagtacaat    6960
gtacacatgg aattaagcca gtagtatcaa ctcaactgct gttaaatggc agtctagcag    7020
aagaagaggt agtaattaga tctgccaatc tcacagacaa tgttaaaacc ataatagtac    7080
agctgaacca atctgtagaa attaattgta caagacccaa caacaataca agaaaaagaa    7140
tccgtatcca gagaggacca gggagaacat tgttacaat aggaaaaata ggaaatatga    7200
gacaagcaca ttgtaacatt agtagagcaa aatggaataa cactttaaaa cagatagcta    7260
gcaaattaag agaacaatat ggaaataata aaacaataat ctttaagcag tcctcaggag    7320
gggacctaga aattgtaacg cacagtttta attgtggagg ggaattttc tactgtaatt    7380 caacacaact gtttaatagt acttggttta atagtacttg gagtactgaa gggtcaaata    7440
acactgaagg aagtgacaca atcacactcc catgcagaat aaaacaaatt ataaacatgt    7500
ggcaggaagt aggaaaagca atgtatgccc ctcccatcag cggacaaatt agatgttcat    7560
caaatattac agggctgcta ttaacaagag atggtggtaa taacaacaat gggtccgaga    7620
tcttcagacc tggaggagga gatatgaggg acaattggag aagtgaatta tataaatata    7680
aagtagtaaa aattgaacca ttaggagtag cacccaccaa ggcaaagaga agagtggtgc    7740
agagagaaaa aagagcagtg ggaataggag ctttgttcct tgggttcttg ggagcagcag    7800
gaagcactat gggcgcagcg tcaatgacgc tgacggtaca ggccagacaa ttattgtctg    7860
```

-continued

```
gtatagtgca gcagcagaac aatttgctga gggctattga ggcgcaacag catctgttgc    7920
aactcacagt atgggcatc aagcagctcc aggcaagaat cctggctgtg gaaagatacc    7980
taaaggatca acagctcctg gggatttggg gttgctctgg aaaactcatt tgcaccactg    8040
ctgtgccttg gaatgctagt tggagtaata atctctgga acagatttgg aatcacacga    8100
cctggatgga gtgggacaga gaaattaaca attacacaag cttaatacac tccttaattg    8160
aagaatcgca aaccaacaa gaaaagaatg aacaagaatt attggaatta gataaatggg    8220
caagtttgtg gaattggttt aacataacaa attggctgtg gtatataaaa atattcataa    8280
tgatagtagg aggcttggta ggtttaagaa tagttttgc tgtactttct atagtgaata    8340
gagttaggca gggacattca ccattatcgt ttcagaccca cctcccaacc ccgggggggac   8400 ccgacaggcc cgaaggaata aagaagaag gtggagagag agacagagac agatccattc    8460
gattagtgaa cggatcctta gcacttatct gggacgatct gcgaagcctg tgcctcttca    8520
gctaccaccg cttgagagac ttactcttga ttgtaacgag gattgtggaa cttctgggac    8580 gcaggggtg ggaagccctc aaatattggt ggaatctcct acagtattgg agtcaggaac    8640
taaagaatag tgctgttagc ttgctcaatg ccacagccat agcagtagct gaggggacag    8700 ataggggttat agaagtagta caaggagctt gtagagctat tcgccacata cctagaagaa    8760
taagacaggg cttggaaagg attttgctat aagatgggtg gcaagtggtc aaaaagtagt    8820
gtgattggat ggcctactgt aagggaaaga atgagacgag ctgagccagc agcagatggg    8880
gtgggagcag catctcaaga cctggaaaaa catggagcaa tcacaagtag caatacagca    8940
gctaccaatg ctgattgtgc ctggctagaa gcacaagagg aggaggaggt gggttttcca    9000
gtcacacctc aggtaccttt aagaccaatg acttacaagg cagctgtaga tcttagccac    9060
tttttaaaag aaaagggggg actggaaggg ctaattcact cccaacgaag acaagatatc    9120
cttgatctgt ggatctacca cacacaaggc tacttccctg attggcagaa ctacacacca    9180
ggaccaggga tcagatatcc actgacctt ggatggtgct acaagctagt accagttgag    9240
ccagagaagt tagaagaagc caacaaagga gagaacacca gcttgttaca ccctgtgagc    9300
ctgcatggaa tggatgaccc ggagagagaa gtgttagagt ggaggtttga cagccgccta    9360
gcatttcatc acgtggcccg agagctgcat ccggagtact tcaagaactg ctgatatcga    9420
gcttgctaca agggactttc cgctggggac tttccaggga ggcgtggcct gggcgggact    9480
ggggagtggc gagccctcag atcctgcata taagcagctg cttttgcct gtactgggtc    9540 tctctggtta gaccagatct gagcctggga gctctctggc tagctaggga acccactgct    9600
taagcctcaa taaagcttgc cttgagtgct caagtagtg tgtgcccgtc tgttgtgtga    9660
ctctggtaac tagagatccc tcagaccctt ttagtcagtg tggaaaatct ctagcaggt    9719
```

<210> SEQ ID NO 3
<211> LENGTH: 3014
<212> TYPE: DNA
<213> ORGANISM: artificial
<220> FEATURE:
<223> OTHER INFORMATION: plasmid with kanamycin, some e coli portions
<220> FEATURE:
<221> NAME/KEY: gene
<222> LOCATION: (662)..(1477)
<223> OTHER INFORMATION: kanamycin resistant gene

<400> SEQUENCE: 3

```
ggcgggccgc tctagactag gtcaataatc aatgtcaaca tggcggtaat gttggacatg      60
```

-continued

| | |
|---|---|
| agccaatata aatgtacata ttatgatatg gatacaacgt atgcaatggc caatagccaa | 120 |
| tctgatgcgg tattttctcc ttacgcatct gtgcggtatt tcacaccgca tatggtgcac | 180 |
| tctcagtaca atctgctctg atgccgcata gttaagccag ccccgacacc cgccaacacc | 240 |
| cgctgacgcg ccctgacggg cttgtctgct cccggcatcc gcttacagac aagctgtgac | 300 |
| cgtctccggg agctgcatgt gtcagaggtt ttcaccgtca tcaccgaaac gcgcgagacg | 360 |
| aaagggcctc gtgatacgcc tatttttata ggttaatgtc atgataataa tggtttctta | 420 |
| gacgtcaggt ggcacttttc ggggaaatgt gcgcggaacc cctatttgtt tatttttcta | 480 |
| aatacattca aatatgtatc cgctcatgag acaataaccc tgataaatgc ttcaataatg | 540 |
| gggggggggg gaaagccacg ttgtgtctca aaatctctga tgttacattg cacaagataa | 600 |
| aaatatatca tcatgaacaa taaaactgtc tgcttacata acagtaata caaggggtgt | 660 |
| tatgagccat attcaacggg aaacgtcttg ctcgaggccg cgattaaatt ccaacatgga | 720 |
| tgctgattta tatgggtata atgggctcg cgataatgtc gggcaatcag gtgcgacaat | 780 |
| ctatcgattg tatgggaagc ccgatgcgcc agagttgttt ctgaaacatg gcaaaggtag | 840 |
| cgttgccaat gatgttacag atgagatggt cagactaaac tggctgacgg aatttatgcc | 900 |
| tcttccgacc atcaagcatt ttatccgtac tcctgatgat gcatggttac tcaccactgc | 960 |
| gatccccggg aaaacagcat tccaggtatt agaagaatat cctgattcag gtgaaaatat | 1020 |
| tgttgatgcg ctggcagtgt tcctgcgccg gttgcattcg attcctgttt gtaattgtcc | 1080 |
| ttttaacagc gatcgcgtat ttcgtctcgc tcaggcgcaa tcacgaatga ataacggttt | 1140 |
| ggttgatgcg agtgattttg atgacgagcg taatggctgg cctgttgaac aagtctggaa | 1200 |
| agaaatgcat aagcttttgc cattctcacc ggattcagtc gtcactcatg gtgatttctc | 1260 |
| acttgataac cttatttttg acgaggggaa attaataggt tgtattgatg ttggacgagt | 1320 |
| cggaatcgca gaccgatacc aggatcttgc catcctatgg aactgcctcg gtgagttttc | 1380 |
| tccttcatta cagaaacggc ttttttcaaaa atatggtatt gataatcctg atatgaataa | 1440 |
| attgcagttt catttgatgc tcgatgagtt tttctaatca gaattggtta attggttgta | 1500 |
| acactggcag agcattacgc tgacttgacg ggacggcggc tttgttgaat aaatcgaact | 1560 |
| tttgctgagt tgaaggatca gatcacgcat cttcccgaca acgcagaccg ttccgtggca | 1620 |
| aagcaaaagt tcaaaatcac caactggtcc acctacaaca aagctctcat caaccgtggc | 1680 |
| tccctcactt tctggctgga tgatgggcg attcaggcct ggtatgagtc agcaacacct | 1740 |
| tcttcacgag gcagacctca gcgccccccc ccccgagtc aggcaactat ggatgaacga | 1800 |
| aatagacaga tcgctgagat aggtgcctca ctgattaagc attggtaact gtcagaccaa | 1860 |
| gtttactcat atatacttta gattgattta aaacttcatt tttaatttaa aaggatctag | 1920 |
| gtgaagatcc ttttttgataa tctcatgacc aaaatccctt aacgtgagtt tcgttccac | 1980 |
| tgagcgtcag accccgtaga aaagatcaaa ggatcttctt gagatccttt ttttctgcgc | 2040 |
| gtaatctgct gcttgcaaac aaaaaaacca ccgctaccag cggtggtttg tttgccggat | 2100 |
| caagagctac caactctttt tccgaaggta actggcttca gcagagcgca gataccaaat | 2160 |
| actgttcttc tagtgtagcc gtagttaggc caccacttca agaactctgt agcaccgcct | 2220 |
| acatacctcg ctctgctaat cctgttacca gtggctgctg ccagtggcga taagtcgtgt | 2280 |
| cttaccgggt tggactcaag acgatagtta ccggataagg cgcagcggtc gggctgaacg | 2340 |
| gggggttcgt gcacacagcc cagcttggag cgaacgacct acaccgaact gagatacctta | 2400 |
| cagcgtgagc tatgagaaag cgccacgctt cccgaaggga gaaaggcgga caggtatccg | 2460 |

```
gtaagcggca gggtcggaac aggagagcgc acgagggagc ttccagggqq aaacgcctgg    2520 tatctttata gtcctgtcgg gtttcgccac ctctgacttg agcgtcgatt tttgtgatgc    2580
tcgtcagggg ggcggagcct atggaaaaac gccagcaacg cggccttttt acggttcctg    2640
gccttttgct ggccttttgc tcacatgttc tttcctgcgt tatcccctga ttctgtggat    2700
aaccgtatta ccgcctttga gtgagctgat accgctcgcc gcagccgaac gaccgagcgc    2760
agcgagtcag tgagcgagga agcggaagaa tgggcatatg ttgccaaact ctaaaccaaa    2820
tactcattct gatgttttaa atgatttgcc ctcccatatg tccttccgag tgagagacac    2880
aaaaaattcc aacacactat tgcaatgaaa ataaatttcc tttattagcc agaagtcaga    2940
tgctcaaggg gcttcatgat gtccccataa ttttggcag agggaaaaag atctggatcc    3000
gcggccgctc taga                                                     3014
```

<210> SEQ ID NO 4
<211> LENGTH: 9719
<212> TYPE: DNA
<213> ORGANISM: Human immunodeficiency virus type 1
<220> FEATURE:
<221> NAME/KEY: LTR
<222> LOCATION: (1)..(630)
<223> OTHER INFORMATION: 5' LTR
<220> FEATURE:
<221> NAME/KEY: LTR
<222> LOCATION: (9083)..(9243)
<223> OTHER INFORMATION: truncated 3' LTR
<220> FEATURE:
<221> NAME/KEY: gene
<222> LOCATION: (8794)..(9246)
<223> OTHER INFORMATION: truncated Nef
<220> FEATURE:
<221> NAME/KEY: protein_bind
<222> LOCATION: (7723)..(8076)
<223> OTHER INFORMATION: RRE
<220> FEATURE:
<221> NAME/KEY: gene
<222> LOCATION: (6222)..(8792)
<223> OTHER INFORMATION: Env
<220> FEATURE:
<221> NAME/KEY: gene
<222> LOCATION: (6062)..(6307)
<223> OTHER INFORMATION: Vpu
<220> FEATURE:
<221> NAME/KEY: gene
<222> LOCATION: (8376)..(8650)
<223> OTHER INFORMATION: Rev2
<220> FEATURE:
<221> NAME/KEY: gene
<222> LOCATION: (5970)..(6045)
<223> OTHER INFORMATION: Rev1
<220> FEATURE:
<221> NAME/KEY: gene
<222> LOCATION: (8376)..(8466)
<223> OTHER INFORMATION: Tat2
<220> FEATURE:
<221> NAME/KEY: gene
<222> LOCATION: (5831)..(6045)
<223> OTHER INFORMATION: Tat1
<220> FEATURE:
<221> NAME/KEY: gene
<222> LOCATION: (5560)..(5850)
<223> OTHER INFORMATION: Vpr
<220> FEATURE:
<221> NAME/KEY: gene
<222> LOCATION: (5042)..(5620)
<223> OTHER INFORMATION: Vif
<220> FEATURE:
<221> NAME/KEY: gene
<222> LOCATION: (2086)..(5097)
<223> OTHER INFORMATION: polymerase: protease, reverse transcriptase, integrase

```
<220> FEATURE:
<221> NAME/KEY: mutation
<222> LOCATION: (4657)..(4659)
<223> OTHER INFORMATION: stop codon inserted
<220> FEATURE:
<221> NAME/KEY: mutation
<222> LOCATION: (4663)..(4665)
<223> OTHER INFORMATION: stop codon inserted
<220> FEATURE:
<221> NAME/KEY: mutation
<222> LOCATION: (4669)..(4675)
<223> OTHER INFORMATION: 7 base pair deletion
<220> FEATURE:
<221> NAME/KEY: mutation
<222> LOCATION: (4679)..(4684)
<223> OTHER INFORMATION: 2 stop  codons inserted
<220> FEATURE:
<221> NAME/KEY: mutation
<222> LOCATION: (4691)..(4693)
<223> OTHER INFORMATION: stop  codon inserted
<220> FEATURE:
<221> NAME/KEY: mutation
<222> LOCATION: (4703)..(4705)
<223> OTHER INFORMATION: stop  codon inserted
<220> FEATURE:
<221> NAME/KEY: mutation
<222> LOCATION: (21)..(21)
<223> OTHER INFORMATION: 1 base pair deletion
<220> FEATURE:
<221> NAME/KEY: mutation
<222> LOCATION: (104)..(104)
<223> OTHER INFORMATION: point mutation from A to G
<220> FEATURE:
<221> NAME/KEY: mutation
<222> LOCATION: (473)..(473)
<223> OTHER INFORMATION: point mutation from A to G
<220> FEATURE:
<221> NAME/KEY: mutation
<222> LOCATION: (8872)..(8872)
<223> OTHER INFORMATION: point mutation from G to C
<220> FEATURE:
<221> NAME/KEY: mutation
<222> LOCATION: (8985)..(8985)
<223> OTHER INFORMATION: point mutation from G to A
<220> FEATURE:
<221> NAME/KEY: mutation
<222> LOCATION: (9244)..(9246)
<223> OTHER INFORMATION: stop codon inserted
<220> FEATURE:
<221> NAME/KEY: gene
<222> LOCATION: (2086)..(5090)
<223> OTHER INFORMATION: polymerase: protease, reverse transcriptase,
      integrase
<220> FEATURE:
<221> NAME/KEY: gene
<222> LOCATION: (791)..(2293)
<223> OTHER INFORMATION: Gag
<220> FEATURE:
<221> NAME/KEY: mutation
<222> LOCATION: (1097)..(1267)
<223> OTHER INFORMATION: 171 base pair deletion
<220> FEATURE:
<221> NAME/KEY: stem_loop
<222> LOCATION: (456)..(531)
<223> OTHER INFORMATION: TAR

<400> SEQUENCE: 4
tggaagggct aattcactcc caacgaagac aagatatcct tgatctgtgg atctaccaca      60
cacaaggcta cttccctgat tggcagaact acacaccagg accagggatc agatatccac     120
tgacctttgg atggtgctac aagctagtac cagttgagcc agagaagtta gaagaagcca     180 acaaggaga gaacaccagc ttgttacacc ctgtgagcct gcatggaatg gatgacccgg      240
agagagaagt gttagagtgg aggtttgaca gccgcctagc atttcatcac gtggcccgag     300
agctgcatcc ggagtacttc aagaactgct gatatcgagc ttgctacaag ggactttccg     360
```

-continued

```
ctggggactt tccagggagg cgtggcctgg gcgggactgg ggagtggcga gccctcagat      420
cctgcatata agcagctgct ttttgcctgt actgggtctc tctggttaga ccagatctga      480
gcctgggagc tctctggcta gctagggaac ccactgctta agcctcaata aagcttgcct      540
tgagtgcttc aagtagtgtg tgcccgtctg ttgtgtgact ctggtaacta gagatccctc      600
agaccctttt agtcagtgtg gaaaatctct agcagtggcg cccgaacagg gacctgaaag      660
cgaaagggaa accagaggag ctctctcgac gcaggactcg gcttgctgaa gcgcgcacgg      720
caagaggcga gggcggcga ctggtgagta cgccaaaaaa ttttgactag cggaggctag      780
aaggagagag atgggtgcga gagcgtcagt attaagcggg ggaaaattag atcgatggga      840
aaaaattcgg ttaaggccag ggggaaagaa aaatataaa ttaaaacata tagtatgggc      900
aagcagggag ctagaacgat tcgcagttaa tcctggcctg ttagaaacat cagaaggctg      960
tagacaaata ctgggacagc tacaaccatc ccttcagaca ggatcagaag aatgtagatc     1020
attatataat acagtagcaa ccctctattg tgtgcatcaa aggatagaga taaaagacac     1080
caaggaagct ttagacaaga taaggaaga gcaaaacaaa agtaagaaaa agcacagca      1140 agcagcagct gacacaggac acagcagtca ggtcagccaa aattacccta tagtgcagaa     1200
catccagggg caaatggtac atcaggccat atcacctaga actttaaatg catgggtaaa     1260
agtagtagaa gagaaggctt tcagcccaga agtaataccc atgttttcag cattatcaga     1320
aggagccacc ccacaagatt taaacaccat gctaaacaca gtggggggac atcaagcagc     1380
catgcaaatg ttaaaagaga ccatcaatga ggaagctgca gaatgggata gagtgcatcc     1440
agtgcatgca gggcctatcg caccaggcca gatgagagaa ccaaggggaa gtgacatagc     1500
aggaactact agtacccttc aggaacaaat aggatggatg acaaataatc cacctatccc     1560
agtaggagaa atttataaaa gatggataat cctgggatta aataagatag taagaatgta     1620
tagccctacc agcattctgg acataagaca aggaccaaaa gaacctttta gagactatgt     1680
agaccggttc tataaaactc taagagccga gcaagcttca caggaggtaa aaaattggat     1740
gacagaaacc ttgttggtcc aaaatgcgaa cccagattgt aagactattt taaaagcatt     1800
gggaccagca gctacattag aagaaatgat gacagcatgt cagggagtgg gaggacccgg     1860
ccataaggca agagttttgg ctgaagcaat gagccaagta acaaattcag ctaccataat     1920
gatgcagaga ggcaatttta ggaaccaaag aaagattgtt aagtgtttca attgtggcaa     1980
agaagggcac atagccagaa attgcagggc ccctaggaaa aagggctgtt ggaaatgtgg     2040
aaaggaagga caccaaatga aagattgtac tgagagacag gctaattttt tagggaagat     2100
ctggccttcc tacaagggaa ggccaggaa ttttcttcag agcagaccag agccaacagc     2160
cccaccagaa gagagcttca ggtctggggt agagacaaca actcccccct cagaagcagga     2220 gccgatagac aaggaactgt atcctttaac ttccctcaga tcactctttg caacgaccc     2280 ctcgtcacaa taaagatagg gggcaacta aaggaagctc tattagatac aggagcagat     2340
gatacagtat tagaagaaat gagtttgcca ggaagatgga aaccaaaaat gatagggga      2400 attggaggtt ttatcaaagt aagacagtat gatcagatac tcatagaaat ctgtggacat     2460
aaagctatag gtacagtatt agtaggacct acacctgtca acataattgg aagaaatctg     2520
ttgactcaga ttggttgcac tttaaatttt cccattagcc ctattgagac tgtaccagta     2580
aaattaaagc caggaatgga tggcccaaaa gttaaacaat ggccattgac agaagaaaaa     2640
ataaaagcat tagtagaaat ttgtacagaa atggaaaagg aagggaaaat ttcaaaaatt     2700
```

```
gggcctgaaa atccatacaa tactccagta tttgccataa agaaaaaaga cagtactaaa    2760
tggagaaaat tagtagattt cagagaactt aataagagaa ctcaagactt ctgggaagtt    2820
caattaggaa taccacatcc cgcagggtta aaaagaaaa aatcagtaac agtactggat     2880
gtgggtgatg catattttc agttcccta gatgaagact tcaggaagta tactgcattt      2940
accataccta gtataaacaa tgagacacca gggattagat atcagtacaa tgtgcttcca    3000
cagggatgga aaggatcacc agcaatattc caaagtagca tgacaaaaat cttagagcct    3060
tttagaaaac aaaatccaga catagttatc tatcaataca tggatgattt gtatgtagga    3120
tctgacttag aaatagggca gcatagaaca aaaatagagg agctgagaca acatctgttg    3180
aggtggggac ttaccacacc agacaaaaaa catcagaaag aacctccatt cctttggatg    3240
ggttatgaac tccatcctga taaatggaca gtacagccta tagtgctgcc agaaaaagac    3300
agctggactg tcaatgacat acagaagtta gtggggaaat tgaattgggc aagtcagatt    3360
tacccaggga ttaaagtaag gcaattatgt aaactcctta gaggaaccaa agcactaaca    3420
gaagtaatac cattaacaga agaagcagag ctagaactgg cagaaaacag agagattcta    3480
aaagaaccag tacatggagt gtattatgac ccatcaaaag acttaatagc agaaatacag    3540
aagcaggggc aaggccaatg gacatatcaa atttatcaag agccatttaa aaatctgaaa    3600
acaggaaaat atgcaagaat gaggggtacc cacactaatg atgtaaaaca attaacagag    3660
gcagtgcaaa aaataaccac cgaaagcata gtaatatggg aaagactcc taaatttaaa     3720 ctacccatac aaaaggaaac atgggaaaca tggtggacag agtattggca agccacctgg    3780
attcctgagt gggagtttgt caataccct cctttagtga aattatggta ccagttagag      3840
aaagaaccca tagtaggagc agaaaccttc tatgtagatg gggcagctaa cagggagact    3900
aaattaggaa aagcaggata tgttactaac aaaggaagac aaaaggttgt cccctaact     3960 aacacaacaa tcagaaaac tgagttacaa gcaatttatc tagctttgca ggattcagga    4020
ttagaagtaa acatagtaac agactcacaa tatgcattag gaatcattca agcacaacca    4080
gataaaagtg aatcagagtt agtcaatcaa ataatagagc agttaataaa aaaggaaaag    4140
gtctatctgg catgggtacc agcacacaaa ggaattggag gaaatgaaca agtagataaa    4200
ttagtcagtg ctggaatcag gaaaatacta tttttagatg gaatagataa ggcccaagat    4260
gaacatgaga aatatcacag taattggaga gcaatggcta gtgattttaa cctgccacct    4320
gtagtagcaa aagaaatagt agccagctgt gataaatgtc agctaaaagg agaagccatg    4380
catggacaag tagactgtag tccaggaata tggcaactag attgtacaca tttagaagga    4440
aaagttatcc tggtagcagt tcatgtagcc agtggatata tagaagcaga agttattcca    4500
gcagaaacag ggcaggaaac agcatatttt cttttaaaat tagcaggaag atggccagta    4560
aaaacaatac atacagacaa tggcagcaat ttcaccagtg ctacggttaa ggccgcctgt    4620
tggtgggcgg gaatcaagca ggaatttgga attccctaca atccccaaag tcaaggagta    4680
gtagaatcta tgaataaaga attaagaaa attataggac aggtaagaga tcaggctgaa    4740
catcttaaga cagcagtaca aatggcagta ttcatccaca atttaaag aaagggggg       4800 attgggggt acagtgcagg ggaaagaata gtagacataa tagcaacaga catacaaact    4860
aaagaattac aaaaacaaat tacaaaaatt caaaattttc gggtttatta cagggacagc    4920
agaaatccac tttggaaagg accagcaaag ctcctctgga aaggtgaagg ggcagtagta    4980
atacaagata atagtgacat aaaagtagtg ccaagaagaa aagcaaagat cattagggat    5040
tatggaaaac agatggcagg tgatgattgt gtggcaagta gacaggatga ggattagaac    5100
```

```
atggaaaagt ttagtaaaac accatatgta tgtttcaggg aaagctaggg gatggtttta    5160
tagacatcac tatgaaagcc cttatccaag aataagttca gaagtacaca tcccactagg    5220
ggatgctaga ttggtaataa caacatattg gggtctgcat acaggagaaa gagactggca    5280
tttgggtcag ggagtctcca tagaatggag gaaaaagaga tatagcacac aagtagaccc    5340
tgaactagca gaccaactaa ttcatctgta ttactttgac tgttttttcag actctgctat    5400 aagaaaggcc ttattaggac acatagttag ccctaggtgt gaatatcaag caggacataa    5460
caaggtagga tctctacaat acttggcact agcagcatta ataacaccaa aaagataaa     5520 gccacctttg cctagtgtta cgaaactgac agaggataga tggaacaagc cccagaagac    5580
caagggccac agagggagcc acacaatgaa tggacactag agcttttaga ggagcttaag    5640
aatgaagctg ttagacattt tcctaggatt tggctccatg gcttagggca acatatctat    5700
gaaacttatg gggatacttg ggcaggagtg gaagccataa taagaattct gcaacaactg    5760
ctgtttaccc atttcagaat tgggtgtcga catagcagaa taggcgttac tcgacagagg    5820
agagcaagaa atggagccag tagatcctag actagagcct tggaagcatc caggaagtca    5880
gcctaaaact gcttgtacca attgctattg taaaaagtgt tgctttcatt gccaagtttg    5940
tttcataaca aaagccttag gcatctccta tggcaggaag aagcggagac agcgacgaag    6000
acctcctcaa agcagtcaga ctcatcaagt ttctctatca aagcagtaag tagtacatgt    6060
aatgcaacct atacaaatag caatagtagc attagtagta gcaataataa tagcaatagt    6120
tgtgtggtcc atagtaatca tagaatatag gaaaatatta agacaaagaa aaatagacag    6180
gttaattgat agactaatag aaagagcaga agacagtggc aatgagagtg aaggagaaat    6240
atcagcactt gcggagatgg gggtggagat ggggcaccat gctccttggg atgttgatga    6300
tttgtagtgc tacagaaaaa ttgtgggtca cagtctatta tggggtacct gtgtggaagg    6360
aagcaaccac cactctattt tgtgcatcag atgctaaagc atatgataca gaggtacata    6420
atgtttgggc cacacatgcc tgtgtaccca cagaccccaa cccacaagaa gtagtattgg    6480
taaatgtgac agaaaatttt aacatgtgga aaaatgatat ggtagaacag atgcatgagg    6540
atataatcag tttatgggat caaagcctaa agccatgtgt aaaattaacc ccactctgtg    6600
ttagtttaaa gtgcactgat ttgaagaatg atactaatac caatagtagt agcgggggaa    6660
tgataatgga gaaggagag ataaaaaact gctctttcaa tatcagcaca agcataagag    6720
gtaaggtgca gaaagaatat gcatttttt taaaacatga tataatacca atagataatg    6780
atactaccag ctatacgttg acaagttgta acacctcagt cattacacag gcctgtccaa    6840
aggtatcctt tgagccaatt cccatacatt attgtgcccc ggctggtttt gcgattctaa    6900
aatgtaataa taagacgttc aatggaacag gaccatgtac aaatgtcagc acagtacaat    6960
gtacacatgg aattaagcca gtagtatcaa ctcaactgct gttaaatggc agtctagcag    7020
aagaagaggt agtaattaga tctgccaatc tcacagacaa tgttaaaacc ataatagtac    7080
agctgaacca atctgtagaa attaattgta caagacccaa caacaataca agaaaaagaa    7140
tccgtatcca gagaggacca gggagaacat ttgttacaat aggaaaaata ggaaatatga    7200
gacaagcaca ttgtaacatt agtagagcaa aatggaataa cactttaaaa cagatagcta    7260
gcaaattaag agaacaatat ggaaataata aaacaataat ctttaagcag tcctcaggag    7320
gggacctaga aattgtaacg cacagtttta attgtggagg ggaattttc tactgtaatt    7380 caacacaact gtttaatagt acttggttta atagtacttg gagtactgaa gggtcaaata    7440
```

```
acactgaagg aagtgacaca atcacactcc catgcagaat aaaacaaatt ataaacatgt   7500
ggcaggaagt aggaaaagca atgtatgccc ctcccatcag cggacaaatt agatgttcat   7560
caaatattac agggctgcta ttaacaagag atggtggtaa taacaacaat gggtccgaga   7620
tcttcagacc tggaggagga gatatgaggg acaattggag aagtgaatta tataaatata   7680
aagtagtaaa aattgaacca ttaggagtag cacccaccaa ggcaaagaga agagtggtgc   7740
agagagaaaa aagagcagtg ggaataggag ctttgttcct tgggttcttg ggagcagcag   7800
gaagcactat gggcgcagcg tcaatgacgc tgacggtaca ggccagacaa ttattgtctg   7860
gtatagtgca gcagcagaac aatttgctga gggctattga ggcgcaacag catctgttgc   7920
aactcacagt atgggcatc aagcagctcc aggcaagaat cctggctgtg gaaagatacc   7980
taaaggatca acagctcctg gggatttggg gttgctctgg aaaactcatt tgcaccactg   8040
ctgtgccttg gaatgctagt tggagtaata atctctgga acagatttgg aatcacacga   8100
cctggatgga gtgggacaga gaattaaca attacacaag cttaatacac tccttaattg   8160
aagaatcgca aaccaacaa gaaaagaatg aacaagaatt attggaatta gataaatggg   8220
caagtttgtg gaattggttt aacataacaa attggctgtg gtatataaaa atattcataa   8280
tgatagtagg aggcttggta ggtttaagaa tagttttgc tgtactttct atagtgaata   8340
gagttaggca gggacattca ccattatcgt ttcagaccca cctcccaacc ccggggggac   8400
ccgacaggcc cgaaggaata agaagaagaag gtggagagag agacagagac agatccattc   8460
gattagtgaa cggatcctta gcacttatct gggacgatct gcgaagcctg tgcctcttca   8520
gctaccaccg cttgagagac ttactcttga ttgtaacgag gattgtggaa cttctgggac   8580 gcaggggtg ggaagccctc aaatattggt ggaatctcct acagtattgg agtcaggaac   8640 taagaatag tgctgttagc ttgctcaatg ccacagccat agcagtagct gaggggacag   8700 ataggttat agaagtagta caaggagctt gtagagctat cgccacata cctagaagaa   8760 taagacaggg cttggaaagg attttgctat aagatgggtg gcaagtggtc aaaaagtagt   8820
gtgattggat ggcctactgt aagggaaaga atgagacgag ctgagccagc agcagatggg   8880
gtgggagcag catctcaaga cctgaaaaaa catggagcaa tcacaagtag caatacagca   8940
gctaccaatg ctgattgtgc ctggctagaa gcacaagagg aggaggaggt gggttttcca   9000
gtcacacctc aggtaccttt aagaccaatg acttacaagg cagctgtaga tcttagccac   9060
tttttaaaag aaaaggggg actggaaggg ctaattcact cccaacgaag acaagatatc   9120
cttgatctgt ggatctacca cacacaaggc tacttccctg attggcagaa ctacacacca   9180
ggaccaggga tcagatatcc actgaccttt ggatggtgct acaagctagt accagttgag   9240
ccagagaagt tagaagaagc caacaaagga gaacacacca gcttgttaca ccctgtgagc   9300
ctgcatggaa tggatgaccc ggagagagaa gtgttagagt ggaggtttga cagccgccta   9360
gcatttcatc acgtggcccg agagctgcat ccggagtact caagaactg ctgatatcga   9420 gcttgctaca agggactttc cgctggggac tttccaggga ggcgtggcct gggcgggact   9480
ggggagtggc gagccctcag atcctgcata taagcagctg cttttttgcct gtactgggtc   9540 tctctggtta gaccagatct gagcctggga gctctctggc tagctaggga acccactgct   9600
taagcctcaa taaagcttgc cttgagtgct tcaagtagtg tgtgcccgtc tgttgtgtga   9660
ctctggtaac tagagatccc tcagaccctt ttagtcagtg tggaaaatct ctagcaggt   9719
```

DNA COMPOSITION AND USES THEREOF

RELATED APPLICATION

This application is a continuation of U.S. Ser. No. 60/440,245 filed Jan. 15, 2003. A corresponding PCT Application, PCT/US2004/000746 is filed concurrently herewith. Both applications are incorporated herein by reference as if set forth in full.

FIELD OF THE INVENTION

The present invention relates to improved DNA sequences that can be used to induce immune responses, and methods for the treatment and prevention of infectious and neoplastic diseases. A plasmid DNA that encodes one or more antigenic genes operably linked to a promoter and a truncated 3' LTR derived from human immunodeficiency virus exhibits both enhanced safety and acceptable efficiency of expression of antigenic proteins.

BACKGROUND OF THE INVENTION

Every form of classical vaccine, namely the use of killed virus, live attenuated virus, and various combinations of subunits of virus, has been tried for the prevention of HIV infection, to no good effect. It had been found that the classical vaccines worked as intended, but that the resulting immune response, an antibody response, was fundamentally unable to inhibit infection in animal models.

The present inventors have shown that, if an antigen is taken up by immune system cells and expressed in the lymphoid organs, different immune responses can be raised, and might have the potential to control the virus. See U.S. Ser. No. 08/803,484 "Methods and Compositions for Therapeutic and Genetic Immunization, filed Feb. 20, 1997 by J. Lisziewicz and F. Lori. The text of that application is incorporated by reference herein as if set forth in full. That application further disclosed that, while any number of antigens, including viral particles, might be used to raise the immune responses, it would be preferable to use a replication-defective virus due to safety considerations. The application explains that replication-defective viral particles themselves have been shown to be ineffective for raising immune responses. Rather than use viral particles, the inventors preferred to use a different material, a plasmid DNA encoding a replication-defective virus. The application discloses various types of replication-defective viruses to select for encoding, and suggests various ways to obtain replication-defective retroviruses, in particular by alteration of the integrase and gag genes. The inventors have demonstrated that a plasmid DNA encoding a replication-defective virus can be made used to induce immune responses, and that furthermore, such materials can be administered topically without the use of needles See U.S. Pat. No. 6,420,176, Method of Delivering Genes into Antigen Presenting Cells, issued Jul. 16, 2002 to Lisziewicz and Lori. The text of this patent is incorporated herein as if set forth in full.

The inventors have also demonstrated that plasmid DNA encoding a replication-defective virus having an altered integrase gene can be used in conjunction with an effective antiviral drug regimen to treat an existing infection. In a situation where antiviral drugs are able to control an infection but not eradicate it, the drugs can be used until the virus replication is controlled, and then the patient can be treated with the plasmid DNA composition. After this therapeutic vaccine treatment, the patient may exhibit enhanced immune system function, and decreased need for drug treatment. (See U.S. Ser. No. 09/863,606 "Therapeutic DNA vaccination," filed May 23, 2001 by Lisziewicz and Lori,). The examples of that application use an experimental plasmid DNA that was not intended for use in humans.

The inventors now describe a new plasmid DNA for the induction of T cell-mediated immune responses, which can be used to make improved DNA formulations. The plasmid DNA comprises one or more DNA sequences encoding antigenic materials operably linked to a promoter and also having a truncated 3' LTR. The promoter is preferably a 5' LTR. The truncated 3' LTR is important because this feature alone renders any retrovirus encoded by the DNA replication-defective. These DNA can be administered to mammals by any of the previously described methods. However, the inventors prefer topical administration, as this method is both efficient and comfortable for the patient.

Plasmid DNA has been used by both the present inventors and others for induction of immune responses against different pathogens, including HIV. For example, U.S. Pat. No. 6,214,804 describes the use of a different DNA composition, specifically a DNA encoding the protein gp120 operably linked to a CMV promoter. As discussed herein, a CMV promoter is a constitutive promoter, which is less efficient than an inducible promoter. Further, there is no disclosure or discussion of the use of a truncated 3' LTR, or the advantages that may be obtained by its use.

In another example, WO 99/43350 (PCT/US99/04128) describes the use of ADP-ribosylating exotoxins as vaccine adjuvants. An advantage of the present invention is that the formulation can be fully comprised of materials having very low toxicity. In yet another example, U.S. Pat. No. 6,348,450 B1 describes the use of adenovirus vectors as adjuvants in combination with DNA vaccines. The reference discloses that such vectors are immunogenic, and are of limited utility where the target individual has already been exposed to such vectors. An advantage of the present invention is that it need not rely on the use of any immunogenic adjuvants. Therefore, unwanted immunogenic responses are minimized.

Other references disclose the use of DNA vaccines in animals. In particular, primate animal models are widely used for studies involving new preventive and therapeutic approaches for HIV infection (Robinson, H. L. (2002). "New hope for an AIDS vaccine." *Nature Rev Immunol* 2(4): 239–50.). In this reference some of the DNA vaccines administered in combination with other vaccines prior to infection have demonstrated inhibition of viral replication after challenge (Robinson 2002). All of the previously described DNA vaccine constructs had a sequence composition of expressing one or more HIV genes operably linked to CMV promoter. None of these constructs were operably linked to an HIV 5' LTR promoter and none of these constructs were operably linked to a truncated 3' LTR. In our previous applications (PCT US97/02933) we have described a novel composition of DNA vaccine that expresses of replication defective viruses that expresses viral genes operably linked to 5' LTR promoter. In this application we further specify the composition of the DNA by operably linking one or more genes to the truncated 3' LTR and a promoter.

BRIEF DESCRIPTION OF DRAWINGS

FIG. 8 Compares the composition of replication- and integration-defective human immunodeficiency virus (HIV) (See LW, Sequence Id. No. 1) and a similarly-modified simian-human immunodeficiency virus (SHIV)(Sequence Id. No. 4). SHIV plasmid DNA was constructed to demonstrate antiviral efficacy using a DNA encoding a replication- and integration-defective virus in SIV-infected macaque model. The HIV construct contains similar mutations in the integrase gene.

SUMMARY OF THE INVENTION

Figure 1:
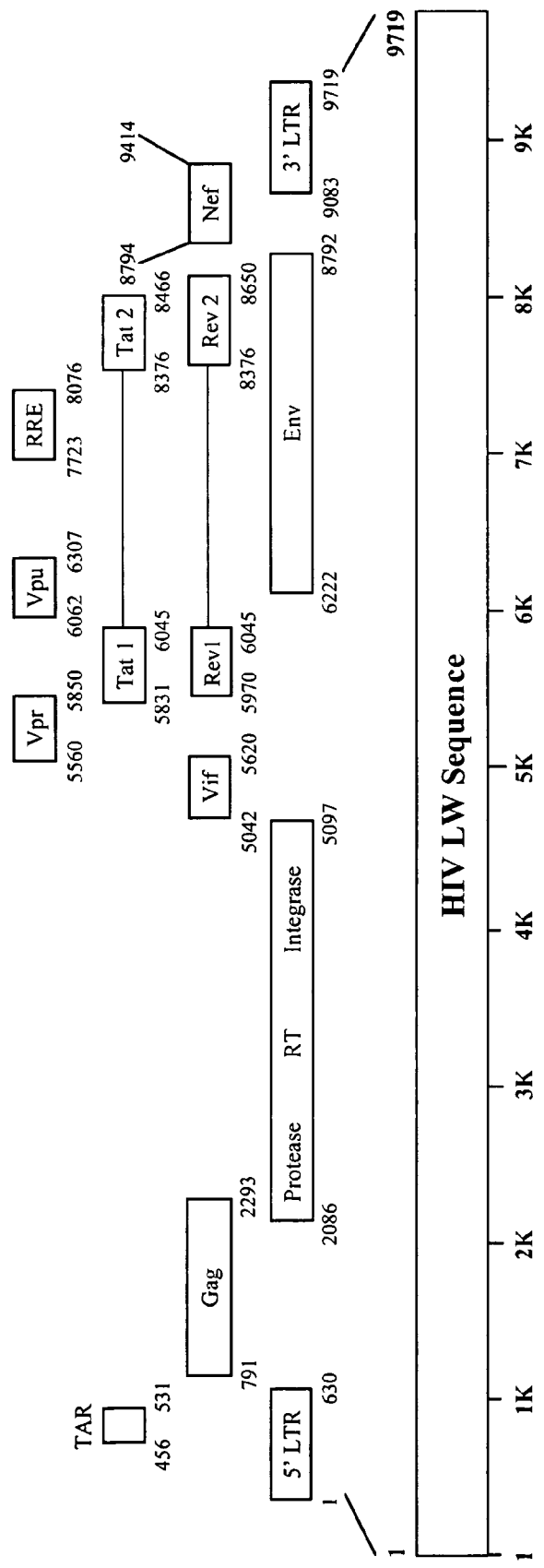
FIG. 1 Composition of the nucleotide sequence of LW (Sequence Id. No. 1). Location of 5' and 3' LTR, genes encoding all HIV proteins and regulatory sequences (TAR, RRE) are indicated.

The present invention relates to improved DNA sequences that can be used to induce immune responses, and methods for the treatment and prevention of infectious and neoplastic diseases. A plasmid DNA that encodes one or more antigenic genes operably linked to a promoter and a truncated 3' LTR derived from human immunodeficiency virus exhibits both enhanced safety and acceptable efficiency of expression of antigenic proteins. The compositions of Sequence Id. Nos. 2 and 3 are particularly preferred for raising an immune response against HIV, as exhibiting enhanced safety due to multiple mutations that do not substantially interfere with efficiency of expression of antigenic proteins. An advantage of the most preferred embodiments is that the constructs mimic the expression and antigen presentation of the wild-type HIV by using an inducible promoter compatible with the target cells and preserving most regulatory genes. An exception is the nef gene, which is substantially preserved for the purpose of producing an immune response, but which is also mutated in a form taken from pediatric long-term survivors. Another advantage is that the preferred embodiments completely inactivate the integrase gene in a manner designed to avoid replication and integration of any potential new viral particles and also avoids the risk that a replication competent virus might emerge from mutation of the constructs or interaction with the patient's own HIV. Yet another advantage is that the most preferred forms of the genes that are used do not exhibit drug resistance. Other benefits and advantages of the present invention will be apparent from the text and examples contained herein.

DETAILED DESCRIPTION OF THE INVENTION

Description of the DNA Construct

In one embodiment, this invention is a DNA construct designed to induce immune responses. The DNA contains one or more genes operably linked with a promoter and has a truncated 3'LTR.

The promoter can be any promoter capable of promoting gene expression in mammals, including for example, constitutive promoters such as CMV and SV-40. Generally constitutive promoters, if they function, will always promote the same level of expression of the affected genes. Inducible promoters are another class, where gene expression is subject to more detailed control. Inducible promoters require the present of some stimulus in order to act. That is, the promoter will not induce gene expression (or will induce very little expression) unless it is activated by the inducer. Further, inducible promoters may be sensitive to the concentration of the inducer. That is, if more of the inducer is present, more gene expression will result. In the preferred embodiment, a promoter induced by the Tat protein, or Tat-inducible promoter, is used. Most preferred is an LTR promoter derived from HIV (HIV-LTR). The LTR does not have to be full length. That is, the 5' end of the LTR can be deleted because it contains only the NRE (negative regulatory elements). The 5' LTR should express gene products efficiently after Tat activation. The advantage of the LTR promoter is that it has a nice balance of efficiency and safety. Tat-induced gene expression is generally more efficient than expression induced by constitutive promoters. However, in the absence of Tat protein there is no (or very low levels of) expression of the genes operably linked to LTR. This mechanism of regulated gene expression mitigates the potential side effects that might originate from a constitutive expression of genes. That is, both the timing and amount of gene expression is more favorably controlled. Another advantage of using Tat-inducible LTR in the present invention is that Tat-inducible LTR is known to be compatible with dendritic cells, and so it a likely candidate to function in a predictable fashion. Further, Tat is also immunogenic, and may contribute to the vaccine's effectiveness.

Figure 3:
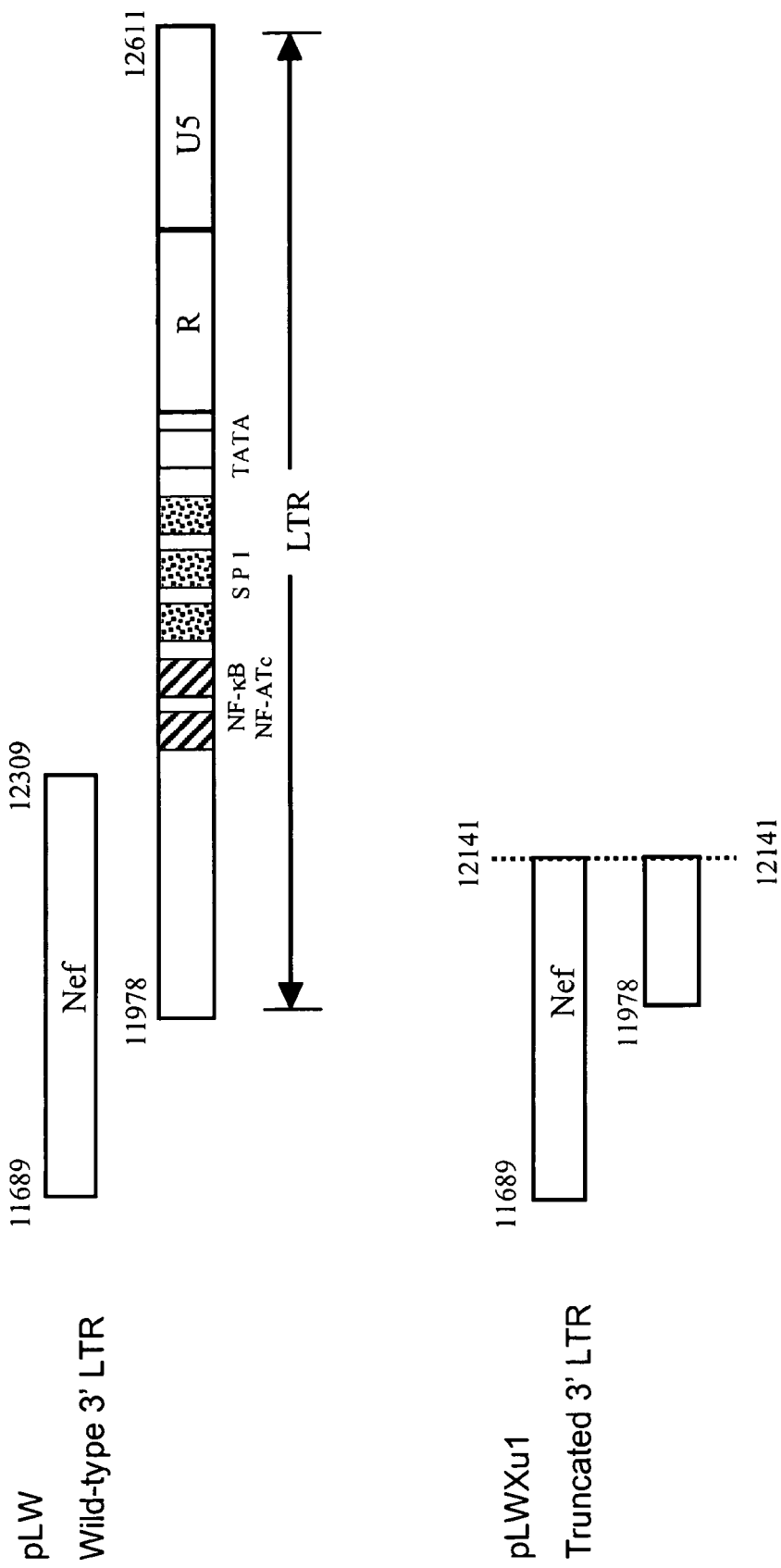
FIG. 3 Detail of pLWXu1 from FIG. 2, showing truncation of the 3' LTR.
Figure 4:
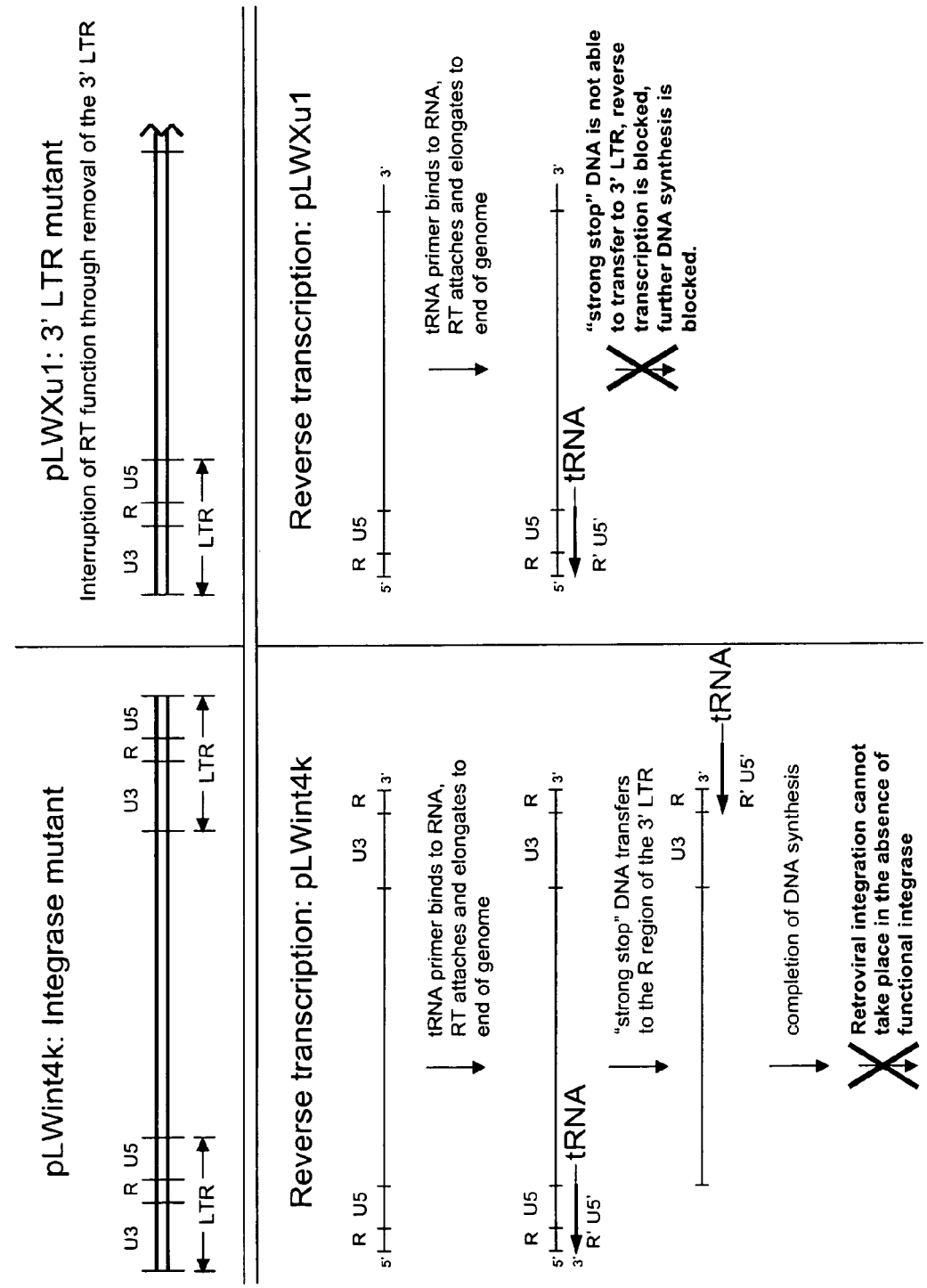
FIG. 4 Diagram of complete inactivation of reverse transcription and integration by the truncated 3' LTR. Example is based on the plasmid pLWXu1. Thick line: DNA; thin line: RNA (Fields, B. N. and D. M. Knipe, Eds. (1990). *Virology*. Retroviridae and their replication. New York, Raven Press, LTD).

The preferred DNA construct also contains a truncated 3' LTR. Normally, a retrovirus has two promoters designated by their locations, 5' and 3'. Normally, 3' LTR functions as a promoter of DNA synthesis in retroviruses. In the present invention, 3'LTR is truncated at least enough to disable it from serving as a promoter. The mutation in the 3'LTR region is important for the safety of the DNA constructs for human use. The most important deletion in the 3' LTR is the deletion of the R region because in the absence of this region reverse transcription and integration of the viral DNA cannot take place (FIG. 3). In the preferred embodiment the deletion involves the R and U5 regions, TATA signal, and also the SP1 and NF-kappaB enhancers (FIG. 3).

The preferred DNA construct encodes genes for immunogenic proteins. Immunogenic proteins originate from viruses, such as HIV, HTLV, Herpes Viruses, influenza viruses, Hepatitis B virus, Hepatitis C virus, Human Papilloma Virus, and from tumors, including oncogens such as MAGE. In one embodiment these genes originate from HIV, and are selected from wild type and mutant versions of the tat, rev, nef, vif, vpr, vpu, env, gag, int, protease, and reverse transcriptase genes. Those of ordinary skill in the art are aware that, in the case of HIV, the genes are highly variable, and that different forms of HIV, called clades, are prevalent in different parts of the world, and may be present, or change from time to time, in a single individual. Therefore, a wide variety of mutations may occur in these genes. The most desired characteristic of these genes is that they contain one or more epitopes of the encoded proteins. An epitope is the minimal portion of an immunogenic protein that is capable of inducing an immune response.

As described above, the genes in the DNA construct can encode mutant proteins. Mutant proteins can be selected to decrease the toxicity or side effects from the wild type protein; improve the efficacy of the DNA construct, or further improve other safety features of the DNA construct.

For example, the wild-type nef protein is known to down-regulate CD4 expression, and may impair immune responses. That is, the wild-type nef protein exhibits toxic effects. Mutations in the nef gene can be selected to decrease the toxicity of the DNA construct. If useful epitopes of mutant nef gene can still be expressed, immune responses against the nef protein can be at least partially preserved.

In another example, the introduction of a dominant negative mutant in the DNA can improve its efficacy, because the expression of such mutant proteins not only induces immune responses but also inhibits virus replication. This class of mutations was originally described for gene therapy purposes and not for the induction of immune responses. However, dominant negative mutant proteins, by definition, inhibit the function of the wild-type protein. Therefore, introduction of dominant negative mutations in one or more genes of the present DNA construct could not only preserve the immune responses against the encoded proteins but also interfere with the replication of the target virus. This new use of dominant negative mutants could be particularly important when the objective is being used to treat an existing infection rather than merely prevent infection. In DNA constructs whose purpose is to induce immune responses against HIV, dominant negative mutants are known, and can be selected at least from the following genes:

i. Envelop (Chen, S. S., A. A. Ferrante, et al. (1996). "Characterization of an envelope mutant of HIV-1 that interferes with viral infectivity." Virology 226(2): 260–8)

ii. Gag (Smythe, J. A., D. Sun, et al. (1994). "A Rev-inducible mutant gag gene stably transferred into T lymphocytes: an approach to gene therapy against human immunodeficiency virus type 1 infection." *Proc Natl Acad Sci USA* 91(9): 3657–61)

iii. Integrase (Yung, E., M. Sorin, et al. (2001). "Inhibition of HIV-1 virion production by a transdominant mutant of integrase interactor 1." *Nat Med* 7(8): 920–6)

iv. Rev (Plavec, I., M. Agarwal, et al. (1997). "High transdominant RevM10 protein levels are required to inhibit HIV-1 replication in cell lines and primary T cells: implication for gene therapy of AIDS." *Gene Ther* 4(2): 128–39)

v. Tat (Fraisier, C., D. A. Abraham, et al. (1998). "Inhibition of Tat-mediated transactivation and HIV replication with Tat mutant and repressor domain fusion proteins." *Gene Ther* 5(7): 946–54)

vi. Vpr (Sawaya, B. E., K. Khalili, et al. (2000). "Transdominant activity of human immunodeficiency virus type 1 Vpr with a mutation at residue R73." *J Virol* 74(10): 4877–81)

vii. Tax (Gitlin, S. D., P. F. Lindholm, et al. (1991). "Transdominant human T-cell lymphotropic virus type I TAX1 mutant that fails to localize to the nucleus." *J Virol* 65(5): 2612–21)

viii. Rex (Bohnlein, S., F. P. Pirker, et al. (1991). "Transdominant repressors for human T-cell leukemia virus type I rex and human immunodeficiency virus type 1 rev function." *J Virol* 65(1): 81–8)

ix. X25 (Smith, C. A. and N. A. DeLuca (1992). "Transdominant inhibition of herpes simplex virus growth in transgenic mice." *Virology* 191(2): 581–8)

x. Mutant ICPO (Chen, J., C. Panagiotidis, et al. (1992). "Multimerization of ICPO, a herpes simplex virus immediate-early protein." *J Virol* 66(9): 5598–602)

Mutant proteins in the DNA construct can also significantly improve the safety of the use of this DNA in human subjects. One safety concern when introducing DNA in virus-infected subjects is that recombination that can theoretically occur between the DNA containing viral genes and the virus. This recombination might generate recombinant replication competent viruses. Using DNA constructs with mutant viral genes can eliminate this risk, because recombinant viruses containing a dominant negative mutation are not only replication-defective but also can inhibit the replication of wild-type viruses.

Description of the Preferred Embodiment of the DNA Construct

In the preferred embodiment the DNA construct is comprised of nucleotide sequences selected from LW (FIG. 1 and Sequence Id. No.1). This construct is preferred for a number of reasons. It contains all of the HIV genes, arranged in the manner of the wild-type virus, so that a broad immune response can be raised, thereby limiting the possibility that the virus might avoid immune system recognition by developing escape mutations. These genes do not contain mutations that confer drug resistance. This is important, as a factor that might preserve the utility of drug treatments. Evidence that this is so can be found in referenes that show that the replication of LW virus can be effectively blocked by conventional antiretroviral therapy (Piccinini, G., A. Foli, et al. (2002). "Complementary antiviral efficacy of hydroxyurea and protease inhibitors in human immunodeficiency virus-infected dendritic cells and lymphocytes." *J Virol* 76(5): 2274–8). This DNA does not contain artificial sequences created in the laboratory, such as codon optimized sequences, so that authentic function has been preserved. Finally, all of the immunogenic proteins expressed by pLW are abundantly expressed in HIV-infected subjects. As a result, the amount of expression of these proteins by the construct is expected to be trivial compared to that of the wild-type virus, and so no new, harmful materials are introduced into the patient by the vaccine.

The Promoter

The promoter in the preferred embodiment is the 5'LTR selected from the sequence of LW (Sequence Id. No. 1). The 5'LTR is located between nucleotides 1 and 630.

Truncated 3' LTR

The truncated 3' LTR in the preferred embodiment is selected from the sequence of LW (Sequence Id. No. 1). The truncation is depicted at the FIG. 3. The truncation of the 3' LTR starts at nt. 9244 in the LW sequence.

Mutant Nef Gene

The preferred truncation of the 3' LTR also results in truncation of the nef gene (FIG. 3), which results in expression of a mutant Nef protein. However, this mutant nef gene is still capable of expressing immunogenic epitopes of Nef, so the DNA constructs containing this mutant are suitable for the induction of Nef-specific immune responses.

Mutant Integrase Gene

Figure 2:
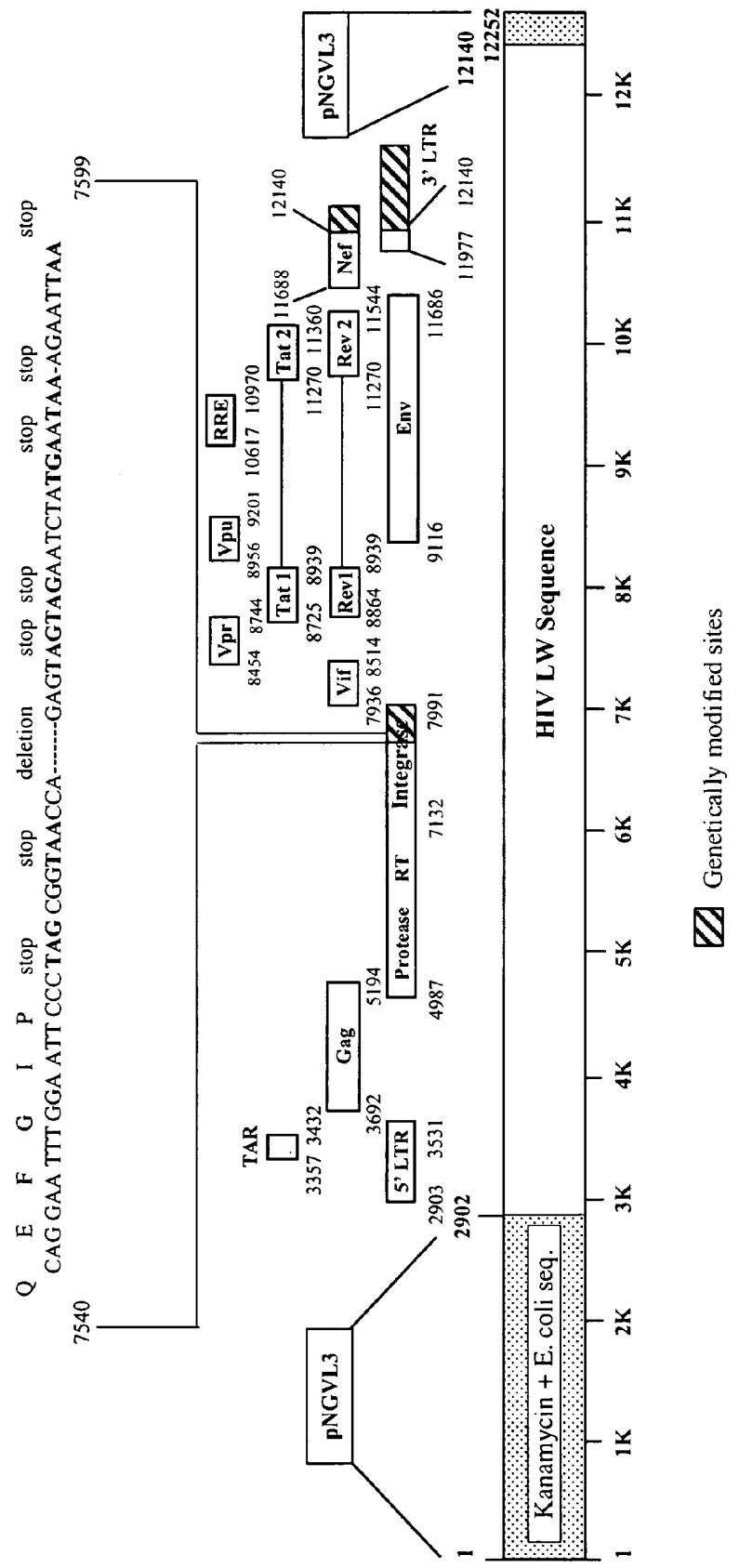
FIG. 2 Composition of the nucleotide sequence of pLWXu1 (Sequence Id. No. 2). This DNA contains sequences required for propagation in *E. coli* as well as the kanamycin resistance gene originating from pNGVL3. Location of 5'LTR and the truncated 3' LTR, genes encoding the wild type regulatory proteins (tat, rev, vpr, vpu, vif) and structural proteins (env, reverse transcriptase, gag, protease), mutant integrase and nef and regulatory sequences (TAR, RRE) are indicated.

The mutant integrase gene in the preferred embodiment is selected from the sequence of LW (Sequence Id. No. 1). The mutation is depicted at FIG. 2. The specific mutations include STOP codons in the open reading frames and a seven base pair deletion. These genetic modifications were carefully designed to avoid potential reversion of the plasmid DNA to the wild type virus. A total of six stop codons were created in the open reading frame of the integrase gene; two by base pair mutations and four by the seven base pair deletion. In addition, the seven base pair deletion created a potential stop codon in the shifted open reading frame and a non-integrase protein product in the other shifted open reading frame. It is highly unlikely that all the six stop codons could simultaneously mutate in vivo and revert to wild type sequences. Even if these six simultaneous mutations were to happen, functional integrase protein would not be reconstituted due to the shifted open reading frame resulting from the seven base pair deletion. This mutant integrase gene is still capable of expressing immunogenic epitopes of integrase, therefore the DNA constructs containing this mutant are suitable for the induction of integrase-specific immune responses.

Mutant Gag Gene

Figure 5:
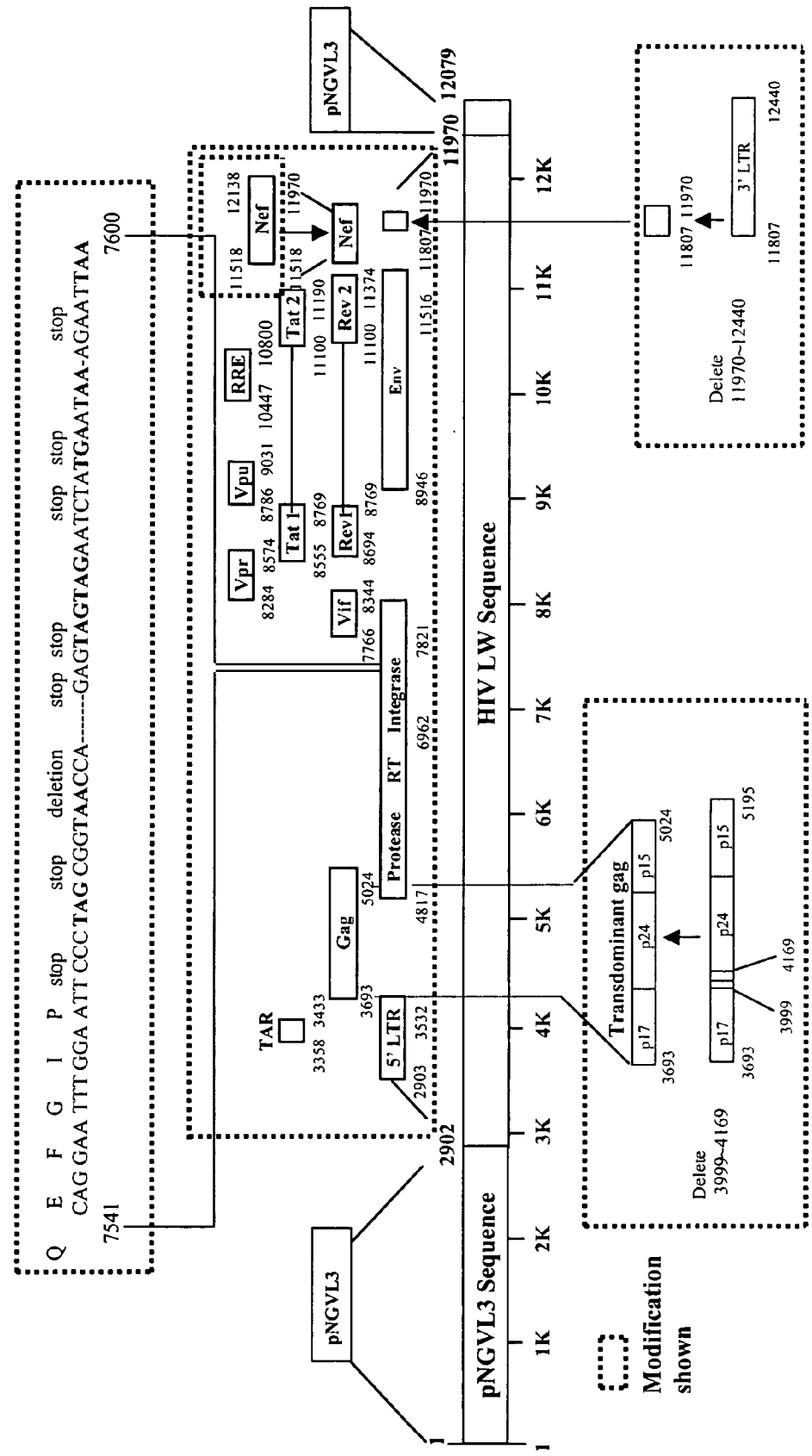
FIG. 5 Composition of the nucleotide sequence of pLWXu2 (Sequence Id. No. 3). The difference between pLWXu1 and pLWXu2 is that pLWXu1 contains a wild-type gag gene and pLWXu 2 contains a mutant gag gene. The mutant gag gene is dominant negative mutant able to inhibit HIV replication.

The mutant gag gene in the preferred embodiment is selected from the sequence of LW (Sequence Id. No. 1). The mutation is depicted at FIG. 5. The specific mutation includes a deletion in the protease cleavage site between p17 and p24. This deletion results in a mutant gag protein that will be incorporated into the viral particle. However, in the absence of protease cleavage virus core and envelope are not separated and the mature viral particle cannot be released. Regarding immunogenicity, the mutant gag still expresses most of the immunogenic epitopes of the gag protein, therefore DNA constructs containing this mutant are suitable for the induction of gag-specific immune responses.

Expression of Structural and Regulatory HIV Proteins

The DNA construct in the preferred embodiment comprises of wild-type structural genes (envelop, reverse transcriptase, protease) and wild-type regulatory genes (tat, rev, vpr, vpu, vif). Expression of these genes can induce immune responses directed against all the epitopes of these genes, therefore the DNA construct is suitable for the induction HIV-specific immune responses with broad specificity.

Detailed Description of the Plasmid pLWXu1

The parental plasmid pLWint4k has already been shown to be both replication-defective and also capable of inducing therapeutic virus-specific immune responses. Because this vaccine is intended for use in humans, further modifications to enhance safety are desired, particularly if these can be achieved without significant loss of efficacy. New plasmid pLWXu1 is pLWint4k with a number of modifications that interrupt the viral life cycle at several points and minimize the probability of reverse transcription, integration, reversion or recombination with the host's HIV-1.

As is the case with pLWint4k, in pLWXu1 the viral gene expression is preferably driven by the 5' HIV-1 LTR, a tat-inducible promoter. A promoter is essential for the efficacy of the product, that is, for efficient expression in dendritic cells and authentic expression and processing of viral proteins, and therefore if no promoter were present the efficacy and the benefit of this therapeutic vaccine will be lost. However, other promoters might be used to replace 5' LTR with similar efficacy.

In human cells, initiation of transcription of the viral RNA is induced by cellular transcription factors (e.g. NFkB). This RNA is transported from the nucleus to the cytoplasm through splicing and these multiple spliced mRNAs are the templates for translation of small viral regulatory proteins (e.g. Tat, Rev, Nef). When the Tat protein translocates back to the nucleus it further activates the transcription of viral RNA.

After efficient transcription in the nucleus, RNA transport to the cytoplasm occurs authentically. First, multiple splicing takes place to produce the mRNA for the regulatory genes. Early expression of these regulatory proteins ensures rapid antigen presentation and initiation of potent immune responses against these less abundant HIV proteins.

After expression of early regulatory proteins Rev transports singly spliced or unspliced RNA to the cytoplasm. These mRNAs encode the structural proteins, Gag, Pol and Env. Antigen presentation of epitopes derived from the most abundant structural proteins therefore occurs later.

CMV or other constitutive promoters cannot achieve in a qualitative and quantitative sense in the following aspects of transcriptional and translational regulation, which are essential for the efficacy of this therapeutic vaccine product:

High level of gene expression. It is known that the HIV-LTR is a stronger promoter in the presence of Tat than CMV (Jayan, G. C., P. Cordelier, et al. (2001). "SV40-derived vectors provide effective transgene expression and inhibition of HIV-1 using constitutive, conditional,and pol III promoters." Gene Ther 8(13): 1033–42).

Gene expression in dendritic cells. It has been demonstrated in vivo, in HIV-1 infected individuals, that HIV-LTR can express genes in dendritic cells (Frankel, S. S., K. Tenner-Racz, et al. (1997). "Active replication of HIV-1 at the lymphoepithelial surface of the tonsil." Am J Pathol 151(1): 89–96).

We believe that the timing of viral antigen presentation (e.g. early expression of regulatory proteins) is very important for the efficacy of the product.

All the regulatory proteins are intact, except the nef gene, which is truncated at the 3' end (FIG. 3). This deletion does not eliminate the major immunogenic epitopes but improves the safety features of the vaccine product. It has been shown that Nef is required for the pathogenicity of HIV-1 (Jamieson, B. D., G. M. Aldrovandi, et al. (1994). "Requirement of human immunodeficiency virus type 1 nef for in vivo replication and pathogenicity." J Virol 68(6): 3478–85; Aldrovandi, G. M., L. Gao, et al. (1998). "Regions of human immunodeficiency virus type 1 nef required for function in vivo." J Virol 72(9): 7032–9). Defective nef genes have been found in pediatric long-term survivors (Geffin, R., D. Wolf, et al. (2000). "Functional and structural defects in HIV type 1 nef genes derived from pediatric long-term survivors." AIDS Res Hum Retroviruses 16(17): 1855–68).

The pLWXu1 plasmid expresses a completely inactivated integrase gene. Integrase is an essential gene for virus replication, We have shown that mutations introduced into integrase gene block viral integration and produces a virus that is not capable of replication and integration (Lisziewicz, J., D. I. Gabrilovich, et al. (2001). "Induction of potent human immunodeficiency virus type 1-specific T-cell-restricted immunity by genetically modified dendritic cells." J Virol 75(16): 7621–8).

We have introduced an extensive 3' U3 deletion (FIGS. 2 and 3) that abolishes viral promoter activity in 3' LTR, thereby preventing the synthesis of a cellular gene located downstream from the 3' LTR (Zufferey, R., T. Dull, et al. (1998). "Self-inactivating lentivirus vector for safe and efficient in vivo gene delivery." J Virol 72(12): 9873–80).

We have deleted the 3' R region and consequently completely impaired reverse transcription (FIG. 2 and FIG. 3), thereby preventing viral DNA synthesis in infected cells. This deletion eliminates the risk that a replication competent virus will emerge from the pLWXu1 plasmid. Importantly, this mutation ensures a higher level of safety than mutating the gene encoding the viral reverse transcriptase (RT) because this defect cannot be rescued in trans by the patient's own HIV.

We have deleted the U5 region, which contains one of the att sites necessary for viral integration (Vicenzi, E., D. S. Dimitrov, et al. (1994). "An integration-defective U5 deletion mutant of human immunodeficiency virus type 1 reverts by eliminating additional long terminal repeat sequences." J Virol 68(12): 7879–90; Zhou, H., G. J. Rainey, et al. (2001). "Substrate sequence selection by retroviral integrase." J Virol 75(3): 1359–70). Besides further decreasing the risk of integration by viral integrase in trans. That is the risk that another virus in the host cell might combine with the vaccine's plasmid or resulting viral particle and supply a functional integrase gene, thereby resulting in the unwanted reacquisition of the ability to integrate. Further, the theoretical possibility of integration by alternative pathways mediated by "integrase-like" enzymes of the host has also been excluded. There is evidence that this region contains essential elements for packaging of viral RNA (Murphy, J. E. and S. P. Goff (1989) "Construction and analysis of deletion mutations in the U5 region of Moloney murine leukemia virus: effects on RNA packaging and reverse transcription." J Virol 63(1): 319–27), therefore the risk of packaging of RNA derived from pLWXu1 is also decreased.

Figure 6:
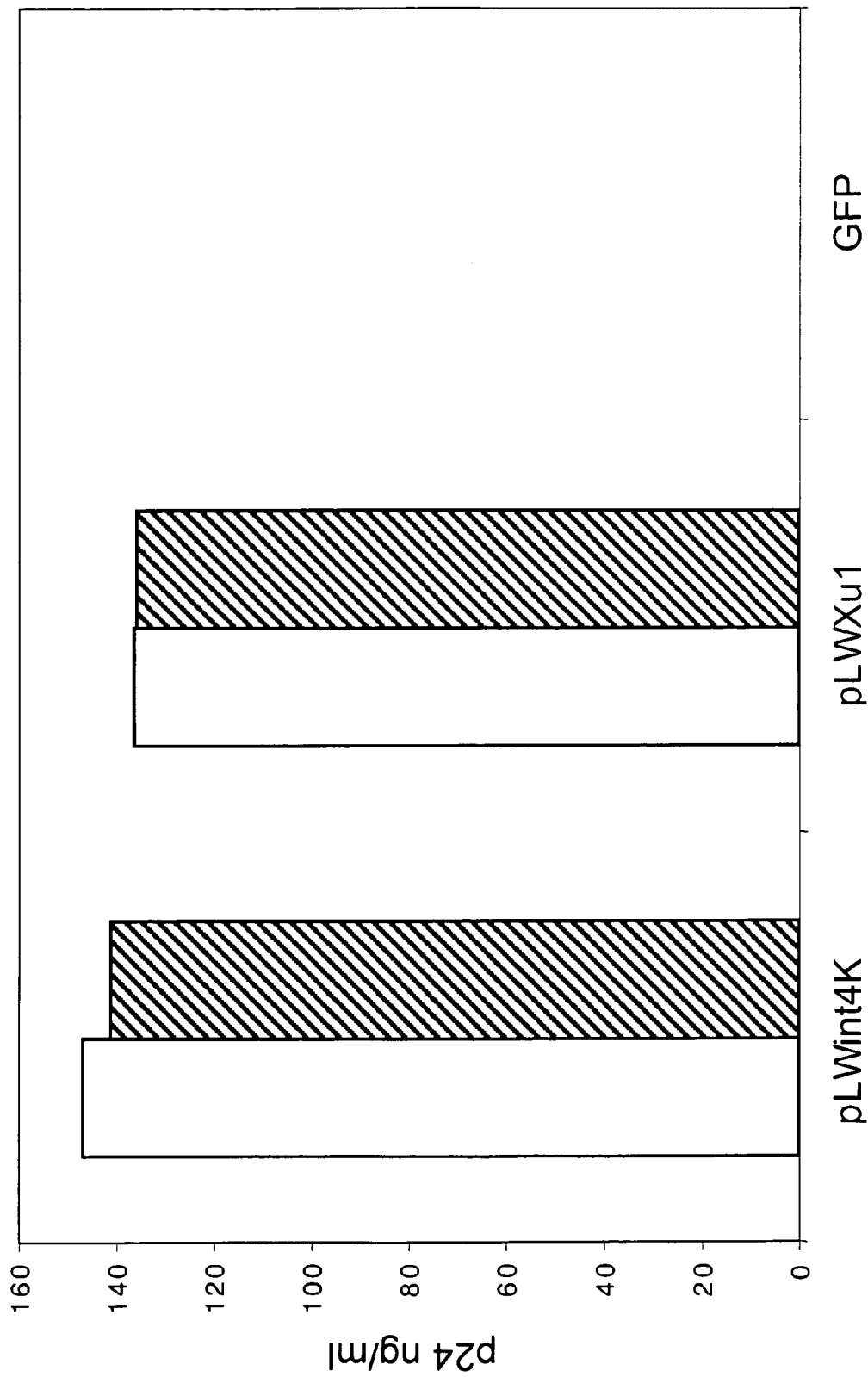
FIG. 6. Compares of gene expression of a prior art integrase mutant DNA (pLWint4K) and new pLWXu1. Both plasmid DNA express HIV proteins efficiently as measured here by quantitative p24 ELISA. The columns represent the median of 3 transfections of T293 cells using the formulated product. Two columns represent 2 independent experiments performed at different time points. Plasmid encoding the green fluorescent protein (GFP, no expression) was used as the negative control.

Due to the various mutations described above, pLWXu1 has improved safety compared to parental plasmid pLWint4k. The improvement of safety features in pLWXu1 does not sacrifice the efficacy of gene expression, because the production of antigenic proteins is very similar, as shown in FIG. 6, which compares p24 expression after transfection of the two plasmids to T293 cells.

Vector Containing the Bacterial Genes

In order to manufacture the DNA in bacterium, the DNA must comprise bacterial sequences required for propagation of the DNA. Since the DNA construct is designed for human use, the Kanamycin gene is inserted for use as a selection marker. In the preferred embodiment the Kanamycin gene and the other bacterial genes were derived from a known vector (pNGVL3) and the CMV promoter sequence present in the original pNGVL3 vector was deleted during the subcloning process (see pLWXu1 at FIG. 2 and Sequence Id. No. 2).

Advantages of the pLWXu1 DNA Construct

This plasmid DNA shows antiretroviral activity, as a result of its features specifically designed for the induction of HIV-specific immune responses:

1. Authentic expression of HIV genes and authentic antigen presentation by dendritic cells to naive T cells mimics 'autovaccination' (Lisziewicz, J., E. Rosenberg, et al. (1999). "Control of HIV despite the discontinuation of antiretroviral therapy." N Engl J Med 340(21): 1683–4; Lori, F., M. G. Lewis, et al. (2000). "Control of SIV rebound through structured treatment interruptions during early infection." Science 290(5496): 1591–3; Rosenberg, E. S., M. Altfeld, et al. (2000). "Immune control of HIV-1 after early treatment of acute infection." Nature 407(6803). The expression of the DNA construct mimics the expression and antigen presentation of wild type HIV, which we believe is essential to provide maximum therapeutic effectiveness.

2. 5' HIV-LTR as the promoter: LTR-driven gene expression is an important feature of the construct to mimic the effect of "autovaccination". This promoter is utilized for viral gene expression and antigen presentation by dendritic cells during primary HIV infection. Moreover, exchanging the LTR to a heterologous promoter (e.g. CMV) would significantly decrease the effectiveness of gene expression.

3. 3' HIV-LTR: This contains an immunogenic part of the nef gene and the transcription stop sequence required for gene expression.

4. Expression of regulatory genes (tat, rev, nef, vpr, vpu, vif): These genes are expressed early, about 24 hours prior to virion production, in infected cells. Cytotoxic T cells that can eliminate infected cells prior to virion production are essential ingredients of a therapy, which is based on inducing HIV-specific T cell immunity.

5. Expression of gag and pol genes: Most of the immunodominant epitopes are located in gag and pol.

6. Expression of tat, rev, vpr, vpu, vif, gag, pol: These genes are the most common between different clades of HIV-1. Immunity against these proteins is not only important to provide antiretroviral activity against different clades of the virus, but also to minimize the chances of immune escape (Barouch, D. H., J. Kunstman, et al. (2002). "Eventual AIDS vaccine failure in a rhesus monkey by viral escape from cytotoxic T lymphocytes." Nature 415(6869): 335–9).

7. Expression of env: The env gene is an important part of the construct because it contains a portion of the open reading frames of the regulatory genes. It also contains the RRE, which is essential for regulation of HIV gene expression in the construct. In addition, expression of env has been shown to improve the effectiveness of vaccines that inhibit virus replication after infection by priming env-specific T helper cells (Robinson, H. L. (2002) "New hope for an AIDS vaccine." Nature Rev Immunol 2(4): 239–50).

Other DNA vaccines developed for the prevention of HIV infection use humanized DNA constructs to encode one or more HIV genes expressed by a heterologous promoter (e.g. CMV). These constructs could introduce new DNA sequences into humans with unknown pathogenic consequences. In contrast, the DNA construct described here allows expression of most HIV antigens in dendritic cells without the need for codon optimization (humanization).

Detailed Description of the Plasmid pLWXu2

Plasmid pLWXu2 is derived from pLWXu1. pLWXu2 contains an additional deletion mutation in the gag gene (FIG. 5). Consequently, pLWXu2 contains all the safety features of pLWXu1 as described above. The specific mutation in gag gene of pLWXu2 includes a deletion (from nucleotides 1097 to 1267 in Sequence Id. No. 1) at the protease cleavage site between p17 and p24. It has been demonstrated that the deletion alone could block the release of HIV virions from the infected cells, thereby interrupting the viral life cycle (Trono, D., M. B. Feinberg, et al. (1989). "HIV-1 gag mutants can dominantly interfere with the replication of the wild-type virus." Cell 59: 113–120.). Therefore, the introduction of the said deletion into gag gene further improves the safety features of pLWXu2.

We found that, the gag deletion resulted in the loss of at least one p24 epitope recognized by ELISA antibody (via Coulter HIV p24 antigen assay), which excludes the determination of gag expression with ELISA. Consequently, a flow cytometry assay using another antibody (KC57, Coulter staining both p24 and its precursor p55 proteins) was employed to determine the expression of the gag gene in pLWXu2-transfected T293 cells. We found efficient HIV gag gene expression with both pLWXu1 and pLWXu2 by flow cytometric assay, suggesting that both of these plasmid DNAs can induce HIV-specific immune responses. However, as shown in Table 1 by the value of mean fluorescence intensity (MFI), pLWXu2 expresses lower amounts of p24 protein than pLWint4k and pLWXu1. It is unclear what is the mechanism that causes the lower amount of expression of the mutant gag in pLWXu2. One possibility is that the mutant gag is unstable and rapidly undergoes degradation, therefore less p24 can be detected by this assay. In this case, pLWXu2 might be more efficient to induce T cell immune responses than pLWXu1 because it has been shown that targeting a protein to a degradation pathway can improve the resulting antigen presentation and T cell activation (Grant, E. P., M. T. Michalek, et al. (1995). "Rate of antigen degradation by the ubiquitin-proteasome pathway influences MHC class I presentation." J Immunol 155(8): 3750–8).

TABLE 1

Mean fluorescence intensity of p24 staining in transfected T293 cells.

| Plasmid used to transfect T293 cells | Mean Fluoresence Intensity in experiment 1 | Mean Fluoresence Intensity in experiment 2 |
| --- | --- | --- |
| No plasmid | No positive cells | No positive cells |
| pLWint4k | 142.5 | 86.4 |
| pLWXu1 | 71.3 | 47.7 |
| pLWXu2 | 19.7 | 8.9 |

Formulation of the DNA Construct

The DNA construct invented here is designed to elicit immune responses. Therefore, this DNA is formulated in a pharmaceutically acceptable composition for the use of induction of immunity. The formulations of the disclosed nucleotide sequences include, but not limited to the following list:

1. Plasmid DNA in water solution
2. Plasmid DNA in physiological salt solution
3. Plasmid DNA in sugar (including glucose) solution
4. Plasmid DNA with transfection facilitating formulation
    a. In complex with viral vectors
    b. Associated with liposomes
    c. Associated with virosomes
    d. In complex with PEI and derivatives (e.g. PEIm)
    e. On gold particles
    f. In cream
    g. In suppository
    h. In pills
    i. Formulated to form particles
    j. Formulated to form particles targeting specific cell types
        i. Formulated to target Langerhans cells
        ii. Formulated to target dendritic cells
5. The disclosed nucleotide sequences can be introduced to viral vectors
    a. Adenovirus vectors
    b. Herpes virus vectors
    c. Adeno-associated virus vectors
    d. Retrovirus vectors
    e. Lentivirus vectors
6. The disclosed nucleotide sequence and the DNA constructs can be introduced into bacteria (bacterial drug formulation)

Preferred Formulation of the DNA Construct is the DermaVir Formulation

We have developed and tested a DNA formulation in primates, and demonstrated the feasibility of using the DNA in combination with presently approved antiretroviral drugs. The preferred formulation ("DermaVir") consists of a plasmid DNA construct, polyethylenimine-mannose (PEIm) and dextrose in a water solution.

PEIm, molecular weight=25–28 kD, is an organic macromolecule with a high cationic-charge-density potential. PEIm complexes the plasmid DNA and forms a particle. This particle mimics a bacteria, because it has a mannosilated surface and can both target epidermal Langerhans cells and facilitate gene expression by those cells.

PEIm is manufactured in five distinct steps or stages:
Step 1. Polymerization of 2-ethyl-2-oxazoline into Poly (2-ethyl-2-oxazoline) (PEOX)
Step 2. Purification of Poly(2-ethyl-2-oxazoline)
Step 3. Conversion of PEO to PEI and Purification of the PEI
Step 4. PEI derivatization to PEI-mannose
Step 5. Purification of PEIm Analytical tests have been developed to characterize PEIm intermediate and end product, demonstrate PEI derivations and potency, and determine purity and relative amine concentration. Each batch of PEIm must pass eleven in-process analytical methods including NMR, Resorcinol-Sulfuric Acid, Gel permeation, endotoxin testing, and transfection of cells prior to release. Each PEIm bulk product lot is assigned a lot number, product number and a Certificate of Analysis.

10% Dextrose, USP

The formulation of DermaVir uses aqueous dextrose. 10% aqueous in 5 ml ampules (Abbott Laboratories, North Chicago, Ill.). The specification is 10% dextrose for injection, USP, a sterile, nonpyrogenic solution (NDC 0074-4089-02), containing no antimicrobial agent or added buffer.

DermaVir Formulation
Three components of DermaVir:
Plasmid DNA in water solution (1 mg/ml),
PEIm (13.6mM),
Dextrose (10%).
Step 1. Prepare Solution A: Combine 0.2 ml PEIm with 0.6 ml dextrose, cap and invert 5 times Step 2. Prepare Unit B: Combine 0.2 ml plasmid DNA with 0.6 ml dextrose, cap and invert 5 times Step 3. Prepare DERMAVIR: Combine Unit A and Unit B, cap and invert 5 times.

Tests and Specifications for Quality Control of DermaVir formulation with pLWXu1

| Procedure Number | Title | Purpose | Method | Specification to Pass |
|---|---|---|---|---|
| OP-2005 | Transfection assay | Determination of the potency of DERMAVIR | Transfection of T293 cells with DERMAVIR | >30 ng/mL of p24 antigen |
| OP-2004 | Stability assay | Determination of the stability of DERMAVIR at room temperature | Transfection assay 24 hours after formulation of DERMAVIR | >30 ng/mL of p24 antigen |
| OP-2007 | Residual charge assay | Determination of the charge of DERMAVIR | Agarose gel electrophoresis | Complete retardation |

The transfection assay is a suitable marker for the potency of the DermaVir formulation, because potency is directly dependent upon expression of the DNA by the transfected cells. The assay measures the potency of a formulation by quantifying a protein, HIV p24, found in the supernatant of a sample after transfection.

We used the pLWXu1 plasmid DNA in the DermaVir formulation, and tested it as follows. T293 cells are plated in Dulbecco's Modified Eagle Medium supplemented with 10% fetal calf serum, 1-glutamine, penicillin, and are removed with trypsin, washed, and plated in a 48-well polystyrene culture plate. Prior to transfection, the media is exchanged for DMEM containing 16 µl DermaVir. Two hours post-transfection, DMEM is refreshed and, after 48 hours culture, supernatants are collected and stored at −20° C. To determine the expression of the DNA, HIV-1 p24 antigen in the supernatants is measured by quantitative ELISA (Coulter HIV-1 p24 Antigen Assay, U.S. License No. 1185). The FDA has licensed this kit for use with tissue culture specimens. Results depicted in FIG. 6 show that pLWXu1 expresses HIV-1 p24 antigen in amounts similar to the control, an integrase mutant DNA, that has been previously shown to elicit immune responses. The pLWXu1, therefore, can be used for the prevention and treatment of HIV.

The Residual Charge Assay measures a feature of the DermaVir formulation that is critical to potency. To be effective, the DNA must form a neutrally charged particle in PEIm/dextrose solution. The test is based upon the fact that neutralized DNA does not migrate from a well during agarose gel electrophoresis. Thus, if a DermaVir formulation does not migrate under a charge (total complexation), the test provides evidence that the DNA in that lot of product is neutral and the product properly formulated. The test involves electorphoresis of 0.01 mL sample of DermaVir formulation in standard 0.8% agarose gel. To visualize the DNA the gels are stained with Ethidium Bromide and migration is measured against a standard.

To date, we have completed 24 hour stability testing of the DermaVir formulations. The DermaVir transfection assay was employed freshly after formulation (0 hours) and after incubation of DermaVir formulation for 24 and 48 hours at room temperature to determine the stability. We found that this formulation is stable at room temperature for 48 hours.

Methods of Administration for the Induction of Immune Responses

The DNA composition invented here is useful for the induction of immune responses in mammals, including human subjects. For this use the formulations of the DNA construct described above can be administered via all typical routes, including topical, intradermal, subcutaneous, intramuscular, oral, rectal, or vaginal. The topical route is most preferred. The vaccine may be administered by a variety of devices, including a single or bifurcated needle gene gun, particle bombardment device, or skinVac device (from Becton Dickinson Biosciences San Jose, Calif. 95131)

Preferred Administration of the DNA Construct is Topical

Figure 7:
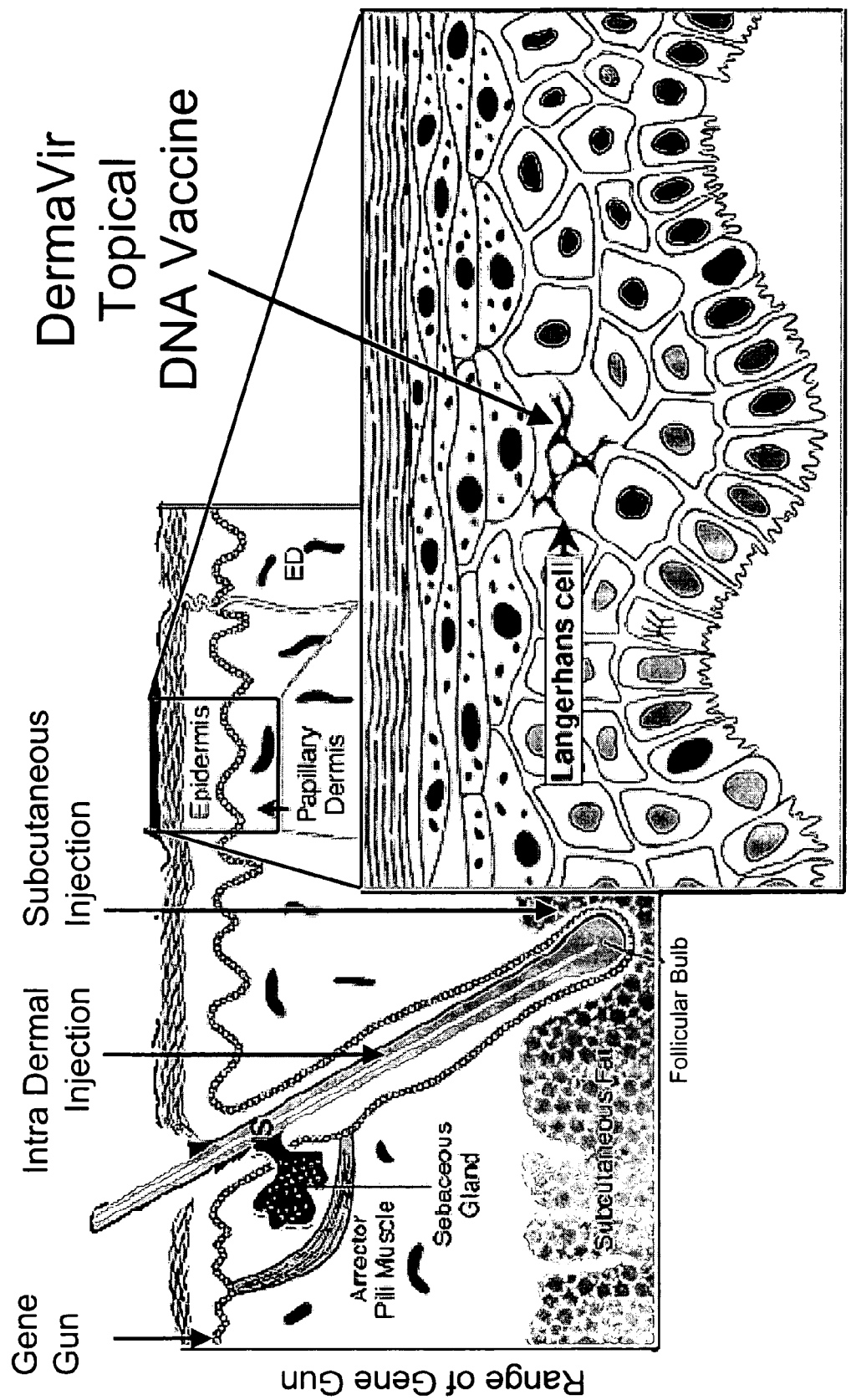
FIG. 7 Compares the way different methods for DNA immunization penetrate the skin to various degrees. Langerhans cells can be found very close to the surface, just under the stratum corneum. Topical administration most closely targets the position of the Langerhans cells.
Figure 9:
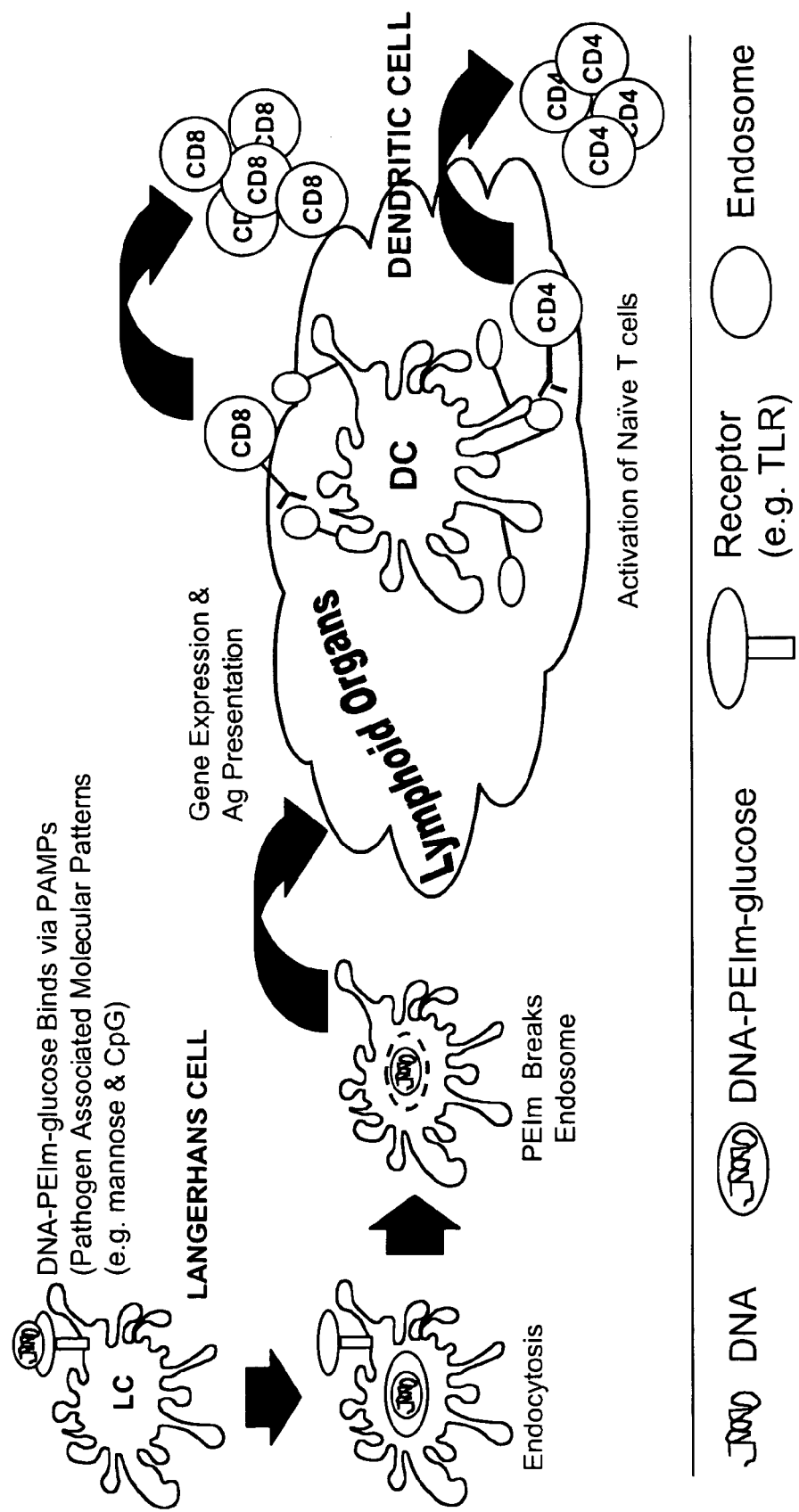
FIG. 9 Describes the mechanism of induction of immune responses after topical immunization using DNA/PEIm/glucose formulation.

It is well established that the injection of DNA capable of expressing immunogenic proteins, like HIV proteins, can induce immune responses. However, less data is available for topical administration. The preferred route of administration of the DNA+PEIm+glucose formulation is topical, because 1. The formulation targets Langerhans cells located under the stratum corneum, therefore needle injection would miss these cells (see FIG. 7).
2. Langerhans cells are the precursor of dendritic cells that migrate to the lymph nodes. Antigen presentation by dendritic cells is important for the induction of effective immune responses.
3. Topical administration of the formulation was not toxic in primates and swine, suggesting the absence of toxicities in human subjects.

After formulation the product should be applied on a prepared skin characterized by a perforated stratum corneum. The perforation allows the DermaVir particle better access the Langerhans cells, which are located just below. Perforation is mild removal of the outermost layer of skin cells, and can be achieved by shaving, clipping, stripping, exfoliating, rubbing, scarifying and scratching the skin. We have used the following method:

1. Identify the sites for vaccination. For example, the left and right upper back (trapezius/suprascapular region) and the ventral aspect of the proximal left and right thigh. Any other vaccination sites covered by skin or mucose can be also used.
2. Gently shave the vaccination sites using a disposable razor.
3. Disinfect the vaccination sites using 70% isopropyl alcohol swabs.
4. Gently abrade the skin surface at the vaccination sites. This could be done by rubbing a Buf-Puf™ exfoliating sponge repeatedly (50 times back and forth) over the area, applying light pressure but taking care not to break the skin. Use a new side of sponge for each site. Other exfoliation methods can be applied here as well, for example using a special device.

5. Apply Tegaderm™ adhesive to each vaccination site and immediately strip off in one quick movement to remove residual cell matter on the skin surface. Repeat if necessary (high dose vaccination) to cover whole area of vaccination site.
6. Repeat taping procedure at a 90° angle to the first taping with the same adhesive.
   a. Using the 1 ml-syringe and needle draw the formulated DNA. Using the 1 ml-syringe (without needle!), apply the vaccine to one site.
7. Distribute the liquid formulation evenly over the vaccination site using the tip of the syringe, taking care to avoid spillage beyond the vaccination site to ensure optimal dosing.
8. Cover the area with the nonabsorbent wound dressing.

Preferred Dose of the DNA Construct in Adult and Pediatric Subjects

Quantitative composition of the dosages form is as follows:

| Dosage | Composition | Total Volume |
|---|---|---|
| Low dose (single application) | 0.1 mg DNA + 0.1 ml 13.6 mM PEIm + 0.6 ml 10% dextrose in water | 0.8 ml |
| Medium dose (single application) | 0.2 mg DNA + 0.2 ml 13.6 mM PEIm + 1.2 ml 10% dextrose in water | 1.6 ml |
| High dose (single application) | 0.4 mg DNA + 0.4 ml 13.6 mM PEIm + 2.4 ml 10% dextrose in water | 3.2 ml |

For adult subjects a total of 0.8 ml issued per low dose DermaVir administration; i.e., 0.2 ml DermaVir per site (four sites per patient). For high dose administration 0.8 ml DermaVir is administered per site (four sites per patient) for a total of 3.2 ml. For pediatric patients Low dose and medium dose is recommended.

The preferred size of the skin surface for vaccination is:
a. Low-dose vaccination: 40 square centimeters
b. Medium-dose vaccination: 80 square centimeters
c. High-dose vaccination: 160 square centimeters Primate SIV Infection and Disease Progression Mimics HIV Infection of Human Subjects The progression of $SIV_{251}$-infection in rhesus macaques as been shown to be similar to, but faster than that of HIV infection in humans. Further, the response of SIV-infected macaques to variations in antiretroviral drug therapies closely follows that of humans. This animal model has been validated in previous studies (Lisziewicz, J., E. Rosenberg, et al. (1999). "Control of HIV despite the discontinuation of antiretroviral therapy." *N Engl J Med* 340(21): 16834; Lori, F., M. G. Lewis, et al. (2000). "Control of SIV rebound through structured treatment interruptions during early infection." *Science* 290(5496): 1591–3; Rosenberg, E. S., M. Altfeld, et al. (2000). "Immune control of HIV-1 after early treatment of acute infection." *Nature* 407(6803): 523–6) and was therefore chosen as the best animal model to study the question of whether particular HIV/AIDS vaccines might have a therapeutic benefit for humans.

Derivation of a Vaccine Formulation

Various molecular clones of HIV and variations thereon are available for scientific study. One such clone, SHIV, was chosen for the primate studies described herein, because it is the closest relative of HIV that causes pathogenic infection in macaques. In addition, SHIV contains an HIV envelope that is heterologous to the $SIV_{251}$ challenge virus; consequently the data obtained using this model can presumably be translated to clinical situations with HIV in man.

A Simian/Human Immunodeficiency Virus (SHIV) construct, that is, a plasmid DNA encoding a Simian/Human Immunodeficiency Virus (SHIV) was made with the same molecular characteristics as the HIV-based plasmid DNA, and used to formulate a DermaVir vaccine (FIG. 8).

The SHIV molecular clone was developed by introducing a mutation in the SHIV integrase gene at the same position as the mutations described above for the HIV vaccine construct, pLWint4K(Sequence Id. No. 1). This yielded the plasmid DNA encoding a replication- and integration-defective SHIV construct pSHIV(int-1) (Sequence Id. No. 4) whose sequence had molecular characteristics very similar to the DNA constructs described in the preferred embodiment (pLWXu1)(Sequence Id. No. 2). Indeed, it contained a deletion, frame shift and three separated stop codons in the open reading frame of the integrase gene and also stop codons in the other reading frame of this region.

Studies in non-human primates with pSHIV(int-1), formulated with polyethylenimine-mannose (PEIm) and a glucose solution (as described above) demonstrated that this topical, therapeutic DNA immunization could induce SIV-specific T cell responses. The quantity of these T cells was associated with clinical, immunological and virological benefit during chronic infection and AIDS. We conducted two separate studies on 26 chronically-infected primates and an additional 10 macaques already showing signs of AIDS (U.S. Ser. No. 09/863,606 and PCT/US02/16546) In one experiment, the monkeys were randomized to receive HAART, (3 weeks on HAART and 3 weeks off), HAART+vaccine and the vaccine alone. The best results were obtained by the HMRT+vaccine group, which progressively controlled viral rebound during treatment interruptions from a median 33,860 copies/ml to <200 copies/ml. All treated cohorts survived significantly longer than the untreated controls. In another experiment, 10 macaques with AIDS started the HAART+vaccine treatment with a significantly higher viral load and suppressed viral rebound from a median of 4,292,260 to <200 copies/mL. Control of viral load in the absence of therapy was associated with augmented SIV-specific CD8 and CD4 T cells as measured by IFN-gamma intracellular cytokine assay. While these experiments do not constitute safety studies, topical DNA vaccination (more than 8 doses at the same skin site) did not show signs of toxic side effects.

These experiments have demonstrated that HIV-specific immune responses can be induced by topical DNA vaccination using the composition described here and that such therapy can result in an immunity that leads to suppression of virus replication. DermaVir, the proposed human therapeutic vaccine, should employ authentic expression of most viral genes and authentic presentation of most viral epitopes by dendritic cells. Consequently, DermaVir treatment by induction of T cells that can eliminate virus infected cells in reservoirs of HIV-infected patients and SIV-infected monkeys. Indeed, products using both pSHIV(int-1) and pLWXu1 meet this criteria. Since the SHIV construct demonstrated antiretroviral effectiveness in SIV-infected macaques, we intend to test the same approach using DermaVir in human subjects.

There will be various modifications, improvements and applications of the disclosed invention that will be apparent to those of skill in the art, and the present application is intended to cover such embodiments.

What is claimed is:

1. A composition comprising the nucleic acid of SEQ ID NO. 2.

2. A composition comprising the nucleic acid of SEQ ID NO. 3.

* * * * *